US011834705B2

United States Patent
Farmer et al.

(10) Patent No.: US 11,834,705 B2
(45) Date of Patent: Dec. 5, 2023

(54) MICROBIAL PRODUCTS AND THEIR USE IN BIOREMEDIATION AND TO REMOVE PARAFFIN AND OTHER CONTAMINATING SUBSTANCES FROM OIL AND GAS PRODUCTION AND PROCESSING EQUIPMENT

(71) Applicant: Locus Solutions IPCo, LLC, Solon, OH (US)

(72) Inventors: Sean Farmer, North Miami Beach, FL (US); Ken Alibek, Solon, OH (US); Kent Adams, Twinsburg, OH (US); Karthik N. Karathur, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 604 days.

(21) Appl. No.: 16/468,350

(22) PCT Filed: Dec. 11, 2017

(86) PCT No.: PCT/US2017/065608
§ 371 (c)(1),
(2) Date: Jun. 11, 2019

(87) PCT Pub. No.: WO2018/107162
PCT Pub. Date: Jun. 14, 2018

(65) Prior Publication Data
US 2021/0363407 A1   Nov. 25, 2021

Related U.S. Application Data

(60) Provisional application No. 62/563,691, filed on Sep. 27, 2017, provisional application No. 62/528,725, (Continued)

(51) Int. Cl.
*C09K 8/52* (2006.01)
*C09K 8/524* (2006.01)
(Continued)

(52) U.S. Cl.
CPC .............. *C12Q 1/6846* (2013.01); *C09K 8/52* (2013.01); *C09K 8/524* (2013.01); *C09K 8/54* (2013.01);
(Continued)

(58) Field of Classification Search
CPC . C09K 8/52; C09K 8/524; C09K 8/54; C09K 8/584; C09K 8/60; C09K 8/602;
(Continued)

(56) References Cited

U.S. PATENT DOCUMENTS 4,332,904 A   6/1982   Kurane et al.
4,450,908 A   5/1984   Hitzman
(Continued)

FOREIGN PATENT DOCUMENTS

CN   102352227 A   2/2012
CN   102766579 A   11/2012
(Continued)

OTHER PUBLICATIONS

Alias, N.H., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.
(Continued)

*Primary Examiner* — Aiqun Li
(74) *Attorney, Agent, or Firm* — SALIWANCHIK, LLOYD & EISENSCHENK

(57) ABSTRACT

The subject invention provides microbe-based products, as well as their use in simultaneously enhancing oil recovery from an oil well while efficiently removing contaminating compositions such as biofilm, scale, paraffin, and/or asphaltenes from oil production equipment and oil-bearing formations. The subject invention can also be used to disperse paraffin and asphaltene precipitates, and to reduce
(Continued)

the viscosity of heavy crude oil. The subject invention further provides materials and methods for bioremediation of hydrocarbon-contaminated sites.

3 Claims, 15 Drawing Sheets

Related U.S. Application Data filed on Jul. 5, 2017, provisional application No. 62/523,021, filed on Jun. 21, 2017, provisional application No. 62/461,985, filed on Feb. 22, 2017, provisional application No. 62/432,611, filed on Dec. 11, 2016.

(51) Int. Cl.
| | |
|---|---|
| C09K 8/584 | (2006.01) |
| C12N 1/16 | (2006.01) |
| C12Q 1/6844 | (2018.01) |
| C09K 8/54 | (2006.01) |
| C09K 8/60 | (2006.01) |
| C10G 32/00 | (2006.01) |
| C40B 40/08 | (2006.01) |
| C40B 50/06 | (2006.01) |

(52) U.S. Cl.
CPC ............. *C09K 8/584* (2013.01); *C09K 8/602* (2013.01); *C10G 32/00* (2013.01); *C12N 1/16* (2013.01); *C09K 2208/32* (2013.01); *C12Y 302/02027* (2013.01); *C40B 40/08* (2013.01); *C40B 50/06* (2013.01)

(58) Field of Classification Search
CPC ............. C09K 2208/32; Y10S 507/929; Y10S 507/931
See application file for complete search history.

(56) References Cited

U.S. PATENT DOCUMENTS

| | | | |
|---|---|---|---|
| 4,522,261 A | 6/1985 | McInerney et al. | |
| 4,905,761 A | 3/1990 | Bryant | |
| 6,033,901 A | 3/2000 | Powell, Jr. | |
| 6,758,270 B1* | 7/2004 | Sunde | E21B 43/20 166/246 |
| 7,022,652 B2* | 4/2006 | Marakov | C09K 8/72 507/141 |
| 7,556,654 B1 | 7/2009 | Nero | |
| 7,681,638 B2 | 3/2010 | Soni et al. | |
| 9,422,470 B2 | 8/2016 | Xu et al. | |
| 9,683,164 B2 | 6/2017 | Gunawan et al. | |
| 10,023,787 B2 | 7/2018 | Benoit et al. | |
| 10,072,208 B2 | 9/2018 | Madduri et al. | |
| 10,190,038 B2 | 1/2019 | Armstrong et al. | |
| 2005/0224230 A1* | 10/2005 | Cobb | E21B 43/16 166/266 |
| 2009/0029879 A1 | 1/2009 | Soni et al. | |
| 2011/0044972 A1 | 2/2011 | Fieldhouse et al. | |
| 2011/0237531 A1 | 9/2011 | Yanagisawa et al. | |
| 2012/0122740 A1 | 5/2012 | Roldan Carrillo et al. | |
| 2013/0062053 A1 | 3/2013 | Kohr et al. | |
| 2013/0324406 A1 | 12/2013 | Chisholm et al. | |
| 2014/0273150 A1 | 9/2014 | Angel | |
| 2014/0305649 A1 | 10/2014 | Tang et al. | |
| 2014/0315765 A1 | 10/2014 | McDaniel | |
| 2014/0360727 A1 | 12/2014 | Milam et al. | |
| 2015/0037302 A1 | 2/2015 | Bralkowski et al. | |
| 2015/0045290 A1 | 2/2015 | Coutte et al. | |
| 2015/0299556 A1* | 10/2015 | Gunawan | C09K 8/528 507/243 |
| 2015/0300139 A1* | 10/2015 | Armstrong | E21B 43/26 166/278 |
| 2016/0083757 A1 | 3/2016 | Fonseca et al. | |
| 2016/0222280 A1 | 8/2016 | Kohr et al. | |
| 2016/0251565 A1 | 9/2016 | Yanagisawa et al. | |
| 2018/0148632 A1* | 5/2018 | Bennett | C09K 8/532 |
| 2018/0282608 A1* | 10/2018 | Gopal | C11D 1/58 |

FOREIGN PATENT DOCUMENTS

| | | |
|---|---|---|
| CN | 104109646 A | 10/2014 |
| CN | 105154050 A | 12/2015 |
| CN | 105567580 A | 5/2016 |
| CN | 105753283 A | 7/2016 |
| EP | 0540074 A1 | 5/1993 |
| WO | 2007129332 A1 | 11/2007 |
| WO | 2010111226 A2 | 9/2010 |
| WO | 2012010407 A1 | 1/2012 |
| WO | 2015038820 A1 | 3/2015 |
| WO | 2015153476 A1 | 10/2015 |
| WO | 2015164327 A1 | 10/2015 |
| WO | 2017044953 A1 | 3/2017 |
| WO | 2018191174 A1 | 10/2018 |

OTHER PUBLICATIONS

Amani, H., et al., "Comparative study of biosurfactant producing bacteria in MEOR applications." Journal of Petroleum Science and Engineering. 2010, 75: 209-214.
De Almeida, D., et al., "Biosurfactants: Promising Molecules for Petroleum Biotechnology Advances." Frontiers in Microbiology, Oct. 2016, 7(1718): 1-14.
De Brito, D., Biosurfactants from renewable raw materials, Universidade do Minho Departamento de Engenharia Biologica, Nov. 2013, pp. 1-93.
De Oliveira, M., et al., "Review: Sophorolipids A Promising Biosurfactant and it's Applications." International Journal of Advanced Biotechnology and Research, 2015, 6(2): 161-174.
Elshafie, A. E., et al., "Sophorolipids Production by Candida bombicola ATCC 22214 and its Potential Application in Microbial Enhanced Oil Recovery." Frontiers in Microbiology, Nov. 2015, 6(1324): 1-11.
El-Sheshtawy, H.S., et al., "Production of biosurfactants by Bacillus licheniformis and Candida albicans for application in microbial enhanced oil recovery." Egyptian Journal of Petroleum, 2016, 25: 293-298.
Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.
Gudina, E., et al., "Biosurfactant-producing and oil-degrading Bacillus subtilis strains enhance oil recovery in laboratory sand-pack columns." Journal of Hazardous Materials, 2013, 261: 106-113.
Kurtzman, C.P., et al., "Production of sophorolipid biosurfactants by multiple species of the *Starmerella (Candida)* bombicola yeast clade." FEMS Microbiol Lett, 2010, 311: 140-146.
Morikawa, M., "Beneficial Biofilm Formation by Industrial Bacteria *Bacillus subtilis* and Related Species." Journal of Bioscience and Bioengineering, 2006, 101(1): 1-8.
Nitschke, M., et al., "Production and properties of a surfactant obtained from Bacillus subtilis grown on cassava wastewater." Bioresource Technology, 2006, 97: 336-341.
Nur, H.A., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.
Pacwa-Plociniczak, M. et al., "Review: Environmental Applications of Biosurfactants: Recent Advances." Int. J. Mol. Sci., 2011, 12: 633-654.
Rocha E Silva, F.C.P., et al., "Yeasts and bacterial biosurfactants as demulsifiers for petroleum derivative in seawater emulsions." AMB Expr., 2007, 7(202): 1-13.
Sen, R., "Biosurfactants: Advances in Experimental Medicine and Biology." Landes Bioscience and Springer Science +Business Media, LLC, 2010, 672: 1-331.

(56) References Cited

OTHER PUBLICATIONS

Sharma, A. et al., "A study on biosurfactant production in *Lactobacillus* and *Bacillus* sp." Int. J. Curr. Microbiol. App. Sci., 2014, 3(11): 723-733.

Silva, R., et al., "Applications of Biosurfactants in the Petroleum Industry and the Remediation of Oil Spills." International Journal of Molecular Sciences, 2014, 15: 12523-12542.

Takahashi, M., et al., "Production of Sophorolipid Glycolipid Biosurfactants from Sugarcane Molasses Using Starmerella bombicola NBRC 10243." Journal of Oleo Science, 2011, 60(5): 267-2733.

Thaniyavarn, J., et al., "Production of Sophorolipid Biosurfactant by Pichia anomala." Bioscience, Biotechnology, and Biochemistry, 2008, 72(8): 2061-2068.

\* cited by examiner

FIG. 7
 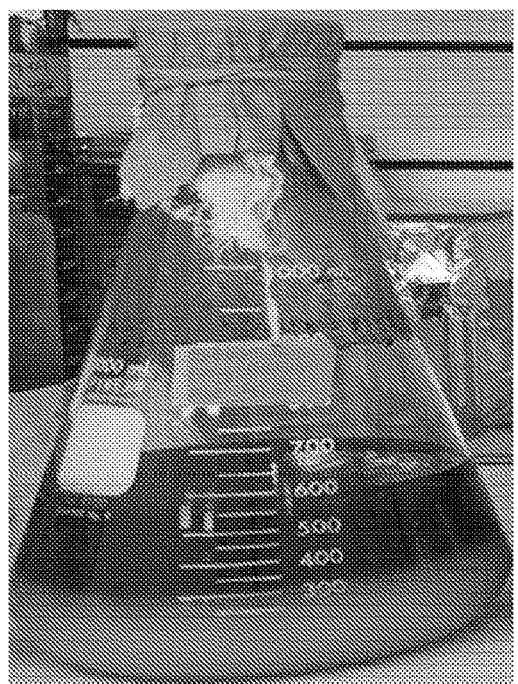
FIG. 8A FIG. 8B

| California heavy crude bottom | Original | Treated | % change |
|---|---|---|---|
| API | -3.7 | 7.2 | 295% increase |
| Viscosity | 2400 cPas | 120 cPas | 95% decrease |//
| Canadian Syncrude | Original | Treated | % change |
| API | 16.2 | 32.08 | 100% increase |
| Viscosity | 455 cPas | 43 cPas | 91% decrease |
| Distressed Mexican Fuel Oil | Original | Treated | % change |
| API | 7.57 | 16.7 | 121% increase |
| Viscosity | 2728 cPas | 887 cPas | 68% decrease |

| | Locus System | Hot Water | Hot Oil | Solvent |
|---|---|---|---|---|
| Removes Paraffin | ☑ | ☑ | ☑ | ☑ |
| Remove Corrosive Bio-films | ☑ | ☒ | ☒ | ☒ |
| Potential Increase in Oil and Gas Production Income | ☑ | ☒ | ☒ | ☒ |
| Reduced LOE through less frequent treatments & stripping jobs | ☑ | ☒ | ☒ | ☒ |
| Cleans Flowlines and Storage Tank Bottoms as part of Treatment | ☑ | ☒ | ☒ | ☒ |
| Environmentally Friendly – No Special Handling Required | ☑ | ☑ | ☒ | ☒ |

| | | Unconsolidated | Alluvial | 100 |
|---|---|---|---|---|
| Cenozoic | | | | |
| Permian | | Limestone/Sandstone/Shale/Coal | Dunkard Monongahela Conemaugh | ~1,300 |
| Pennsylvanian | | | | |
| Mississippian | | Limestone/Sandstone/Shale | Logan Cuyahoga Sunbury, Berea, Bedford | ~800 |
| Devonian | | Shale | Ohio | 1,100 |
| | | Shale/Limestone | Hamilton/Onondaga | 500 |
| | | Limestone/Sandstone | Salina/Bass Islands/Oriskany | 200 |
| Silurian | | Dolomite | Newburg/Lockport | 400 |
| | | Shale | Rochester | 500 |
| | | Limestone/Sandstone | Medina/Clinton/Dayton | 200 |
| Ordovician | | Shale | Juniata | 200 |
| | | Shale | Reedsville | 1,000 |
| | | Limestone | Trenton/Pt. Pleasant | 100 |
| | | Limestone/Dolomite | Black River | 650 |
| | | Dolomite | Wells Creek | 100 |
| | | Dolomite | Beekmantown | 500 |
| | | Sandstone | Rose Run | 150 |
| | | Dolomite | Copper Ridge | 700 |
| Cambrian | | Dolomite/Shale | Conasauga/Nolichucky | 200 |
| | | Dolomite | Rome/Maryville | 500 |
| | | Sandstone | Basal Sandstone | 50-100 |
| Precambrian | | Gneiss | (Precambrian) | — |

- Pennsylvanian Aged Sandstones
  - Speechley Sandstone – 2400', 10-14% Porosity
  - Nineveh Sandstone – 1500', 8-12% Porosity

- Mississippian Aged Sandstones
  - Berea Sandstone – 1500', 10-12% Porosity

- Devonian Aged Sandstones
  - Gordon/Gantz – 1500', 8-10% Porosity

- Silurian Aged Sandstones
  - Clinton Sandstone – 3500-6000', 7-10% Porosity

- Cambrian-Ordovician Aged Sandstones & Dolomite
  - Rose Run Sandstone – 6500-7000', 8-12% Porosity
  - Trempealeau Dolomite – 2500', 10-15% Porosity

FIG. 21

MICROBIAL PRODUCTS AND THEIR USE IN BIOREMEDIATION AND TO REMOVE PARAFFIN AND OTHER CONTAMINATING SUBSTANCES FROM OIL AND GAS PRODUCTION AND PROCESSING EQUIPMENT

This application is a National Stage Application of International Application No. PCT/US2017/065608, filed Dec. 11, 2017; which claims the benefit of U.S. Provisional Application Ser. No. 62/432,611, filed Dec. 11, 2016, U.S. Provisional Application Ser. No. 62/461,985, filed Feb. 22, 2017, U.S. Provisional Application Ser. No. 62/563,691, filed Sep. 27, 2017, U.S. Provisional Application Ser. No. 62/523,021, filed Jun. 21, 2017, and U.S. Provisional Application Ser. No. 62/528,725, filed Jul. 5, 2017, all of which are incorporated herein by reference in their entireties.

BACKGROUND OF THE INVENTION

Oil exists in small pores and narrow fissures within the body of reservoir rocks underneath the surface of the earth. Natural pressure of the reservoir causes the oil to flow up to the surface, thereby providing primary production; however as oil production progresses, the reservoir pressure is depleted to a point at which artificial lift or pumping is required to maintain an economical oil production rate.

When it is necessary to provide external energy for the reservoir to achieve additional oil recovery (secondary recovery), the extra energy can be introduced by injecting gas (gas injection) and/or water (water flooding). After some years of operation in a field, the injected fluids flow preferentially along high permeable layers that cause these fluids to by-pass oil saturated areas in the reservoir. Therefore, an increasing quantity of water (or gas) rises with the oil. By decreasing the ratio of oil to water, it eventually becomes uneconomical to continue the process and the field must be abandoned. In this situation, a third stage of oil recovery, so-called tertiary production or Enhanced Oil Recovery (EOR) can be considered.

At this tertiary stage, technically advanced methods are employed to either modify the properties of reservoir fluids or the reservoir rock characteristics. In general, the methods can be classified into four main categories as thermal methods, chemical methods, miscible or solvent injection, and microbial methods.

Microbial Enhanced Oil Recovery (MEOR) is a multi-disciplinary field incorporating, among others: geology, chemistry, microbiology, fluid mechanics, petroleum engineering, environmental engineering and chemical engineering. The microbial processes proceeding in MEOR can be classified according to the oil production problem in the field: well bore clean-up, which removes mud and other debris blocking the channels where oil flows; well stimulation, which improves the flow of oil from the drainage area into the well bore; and enhanced water floods, which increase microbial activity by injecting selected microbes and sometimes nutrients.

Thus, MEOR uses microorganisms and/or their metabolites to enhance the recovery of residual oil. In this method, nutrients and suitable bacteria, which preferably grow under the anaerobic reservoir conditions, are injected into the reservoir. Microbial by-products that can include biosurfactants, biopolymers, acids, solvents, gases, and enzymes modify the properties of the oil and the interactions between oil, water, and the porous media, thereby increasing the mobility, and consequently the recovery, of oil.

Microorganisms can also be useful in the maintenance of equipment and structures used in oil recovery, transmission, and transport. One of the most common issues leading to structural failure and production inefficiency is the formation of deposits in and around the wellbore, tubing, flow lines, storage tanks, separators, and other components of oil and gas production infrastructure.

The safe and efficient production of hydrocarbon compositions depends on the proper functioning of hydrocarbon-producing facilities. One of the most common issues leading to structural failure and production inefficiency is the formation of deposits in and around the wellbore, tubing, flow lines, storage tanks, separators, and other components of oil and gas production infrastructure.

These problematic deposits are formed by, for example, high-molecular-weight constituents of petroleum fluids, most notably, paraffins and asphaltenes. Loss of solubility in crude oil generally causes the paraffins and asphaltenes to precipitate and form deposits. These can mix with mineral components to form scale. The formation of scale and other deposits can arise from, for example, changes in the pressure, composition and/or temperature of the crude oil.

Systematic treatment or removal of deposits is crucial to maintaining properly functioning hydrocarbon-producing facilities. Once even a thin layer of paraffin or asphaltene deposit is formed on a surface, the rate of further accumulation drastically increases. Furthermore, as a well ages, paraffin and asphaltene-related problems become more prevalent. Additionally, oil production decreases as reservoir pressure drops, which in turn decreases flow rates. Films and chemicals build up with time in the pores of the shale, reducing hydrocarbon movement into the wellbore. This can lead to changes in temperature gradients and thus greater heavy hydrocarbon accumulation.

As the thickness of deposits increases in production and distribution structures over time, the result is a gradual decrease in production. In tubing and casing structures, the deposits begin to reduce the inner diameter of piping and restrict the free flow of oil and gas. As this occurs, the interior roughness of the structures also increases, which raises the pump pressure required to move the petroleum product. If left untreated, deposits can ultimately lead to complete blockage. Furthermore, depending upon the location of the precipitation, maintenance and/or emergency repairs can become extremely expensive.

Current methods of deposit removal fall within four main categories: mechanical, chemical, microbial, and thermal removal. Mechanical removal typically involves the use of scrapers or cutters to physically remove deposits. For example, in tanks where precipitation has occurred, the sides of the tank must be cut out and force, e.g., a sledgehammer, is then used to remove the deposits. For pipelines, complete replacement of pipes is often required if deposits become too thick for manual or mechanical removal.

Chemical removal involves the use of solvents or surfactants that can solubilize deposits or interfere with their crystallization and formation. Examples of widely-used solvents include toluene and xylene. While these chemical solvents help inhibit the precipitation of paraffins and asphaltenes, they cannot prevent precipitation from occurring.

Furthermore, certain strains of bacteria can be used to degrade deposits themselves, or can produce natural biosurfactants that do so. Along with these methods, however, thorough removal of deposits often requires the addition of some type of thermal treatment as well. Thermal removal, with steam or hot oil for example, is useful for melting or dissolving deposits, and as noted, for supplementing other methods of removal.

The presence of large amounts of high molecular weight organic compounds in crude oil itself can also contribute to difficulties in production and transportation of oil. This is due to the effect of, for example, asphaltene content on the viscosity of oil. The greater the content of asphaltenes, paraffins and resins in oil, the greater the viscosity and density of the oil. Viscosity is a critical rheological property of fluids in an oil reservoir, and can greatly affect the ability of the fluid to move from the reservoir and through production systems. Heavy and extra heavy oil, tar and/or asphalt are highly viscous, and thus, highly burdensome to extract and transport.

Forty percent of the world's total oil reserves are heavy and extra heavy oil, accounting for 3.6-5.2 trillion bbl of oil. Thus, recovery of these highly viscous hydrocarbons could have major economic significance. Nonetheless, most heavy and extra heavy oils are not recoverable by conventional methods. For example, a significant amount of energy is required to pump oil with higher viscosity through pipelines to refineries and processing facilities. Furthermore, viscosity affects the speed at which crude oil can be pumped, with more viscous oils contributing to a decrease in overall productivity for an oil field.

Biofilms can also build up in various structures and processing mechanisms, including shale formation facing, wells, pipes, and tanks. "Biofilm" comprises layers of biomass made up of a compact grouping of microorganisms surrounded by an extracellular matrix of polymeric substances. Biofilms adhere to surfaces of many man-made mechanisms, such as tubes and pipes, and can significantly impair their proper functioning. Furthermore, many of the biofilms present in, or on, oil rigs contain sulfate-reducing bacteria that generate potent chemical byproducts, e.g., hydrogen sulfide. Hydrogen sulfide gas is harmful for drill workers who might breathe it. Additionally, hydrogen sulfide can cause corrosion of various mechanisms within an oil producing structure. Furthermore, hydrogen sulfide can cause the souring of oil during storage or transport. Sour oil contains a high sulfur content, which increases costs for producers and consumers due to the increase of time and resources required for processing the oil.

Accumulation of organic deposits in oil and on oil processing equipment can have a compounding effect. Unless these organic compounds are removed, operators can be faced with lowering yields, improper function of pumps, blocked tubing and pipes, and potential for total loss of production. Cost, safety in processing, large-scale sustainability, and damage to formations must be accounted for when developing methods for removing these deposits to ensure long-term efficiency of hydrocarbon production.

Because of the importance of safe and efficient oil and gas production and the difficulties caused by organic compounds, deposits and biofilms in production and transport of oil and gas, there is a continuing need for improved methods of preventing the presence of, and/or removing such contaminants from, hydrocarbon-producing facilities.

BRIEF SUMMARY OF THE INVENTION

The subject invention provides microbes, as well as by-products of their growth, such as biosurfactants and/or enzymes. The subject invention also provides methods of using these microbes and their by-products. Advantageously, the microbe-based products and methods of the subject invention are environmentally-friendly, operational-friendly and cost-effective.

In one embodiment, the subject invention provides microbe-based products, as well as their use in enhancing oil well performance while removing contaminating compositions such as biofilm, scale, paraffin, and/or asphaltene from oil production equipment.

The subject invention further provides materials and methods for bioremediation of hydrocarbon-contaminated sites.

In certain embodiments, the subject invention provides a method for improving oil production efficiency by applying to an oil well a composition having a cultivated yeast microbe and/or a growth product thereof. Advantageously, the subject method works to simultaneously stimulate the oil well while removing paraffin, asphaltenes, scale, and/or other contaminants from the well and oil production equipment.

In one embodiment, methods are provided for treating, for example, a borehole; an oilfield; transportation, transmission, and/or oil refinery equipment; and/or a remediation site. In certain embodiments, the methods are used to improve oil production, as well as maintenance of, for example, pipes, drills, tanks and other structures and equipment involved in oil and/or gas production, transportation, storage and/or refining.

In specific embodiments, the subject invention provides efficient methods for paraffin and/or asphaltene removal by utilizing biochemical-producing microbes. The biochemicals produced by the microbes may be, for example, biosurfactants. In additional embodiments, the compositions and methods of the subject invention can liquefy solid paraffin and/or asphaltene, as well as disperse paraffin and/or asphaltene that has precipitated from oil. Even further, the compositions and methods can simultaneously enhance oil recovery by, for example, improving the flow of oil from a well. This can even be achieved in under-producing stripper (marginal) wells.

In further embodiments, the materials and methods can be used for bioremediation, including bioremediation of hydrocarbon-contaminated waters, soils, and other sites.

In some embodiments, the method utilizes yeast strains and/or by-products of their growth. In one embodiment, the microbe used in the methods of the subject invention is a biosurfactant-producing yeast. The invention provides, for example, a microbe-based product comprising cultivated *Starmerella bombicola* ATCC 22214 and/or products of the growth of that microbe. In addition, the invention provides a microbe-based product comprising cultivated killer yeast strains such as, for example, *Wickerhamomyces anomalus* (*Pichia anomala*) yeast and/or its growth byproducts. In some embodiments, the microbial strain can be used in conjunction with other chemical and/or microbial treatments, including with other species and/or strains of microbe.

In certain embodiments, the microbe-based composition of the subject invention comprises microorganisms and biosurfactants. The biosurfactants can be those produced by the microorganisms themselves, or the biosurfactants can be added in a crude and/or purified form. In some embodiments, the composition further comprises an ionic or semi-ionic liquid.

In some embodiments, the composition further comprises one or more baker's or brewer's yeast (*Saccharomyces cerevisiae*), yeast extracts, salts, and/or solvents.

In certain embodiments, the biosurfactants work synergistically with solvents and other metabolites that are also produced by the microbes.

In certain embodiments, the compositions of the subject invention have advantages over, for example, biosurfactants alone, due to the use of the entire cell culture. These advantages can include one or more of the following: high concentrations of mannoprotein as a part of a yeast cell wall's outer surface; the presence of beta-glucan in yeast cell walls; the presence of biosurfactants in the culture; and the presence of metabolites (e.g., lactic acid, ethanol, beta-glucan, etc.). In certain embodiments, the metabolites serve as solvents.

In one embodiment, the subject invention provides methods of producing a microbial metabolite by cultivating a microbe strain under conditions appropriate for growth and surfactant production; and purifying the metabolite. Examples of microbial metabolites according to the subject invention comprise biosurfactants, biopolymers, solvents, enzymes, proteins, acids, gases, toxins, alcohols, vitamins, minerals, microelements, and amino acids. In a preferred embodiment, the metabolite is a biosurfactant.

The microbe-based products of the subject invention can be used in a variety of unique settings because of, for example, the ability to efficiently deliver: fresh fermentation broth with active metabolites; a mixture of cells, spores and/or mycelia and fermentation broth; a composition with vegetative cells, spores and/or mycelia; compositions with a high density of cells, including vegetative cells, spores and/or mycelia; microbe-based products on short-order; and microbe-based products in remote locations.

BRIEF DESCRIPTION OF THE FIGURES

FIG. 7 shows each of the flasks in FIGS. 1-5, after 5 hours of shaking.

FIGS. 8A-8B show the upgrading of petcoke using the subject invention. 8A shows a container of rock hard petcoke, requiring the use of a hammer to break loose. 8B shows the petcoke, liquefied after only a few hours of treatment with the subject invention.

FIG. 21 shows the range of geologies, depths, permeabilities and temperatures where the subject invention has been successful for treatment of paraffin and asphaltene.

DETAILED DESCRIPTION

Figure 1A:
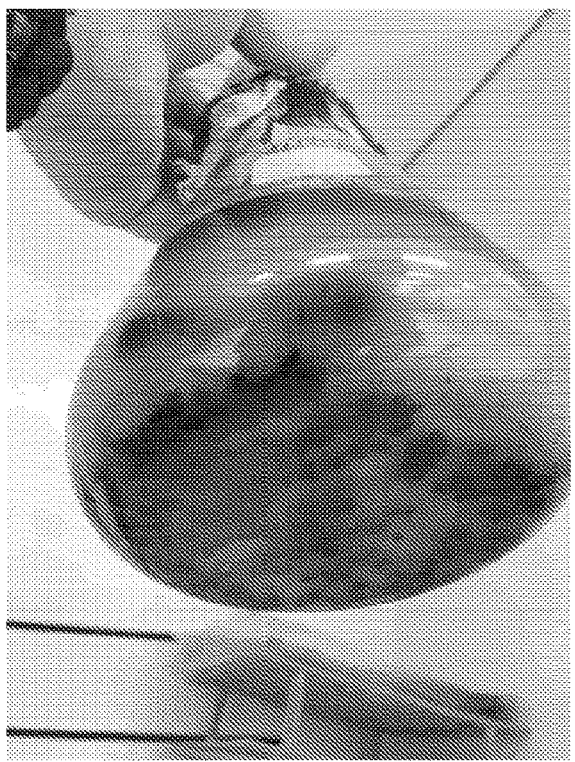
FIGS. 1A-1B show 100 g of asphaltene precipitate in Star 3+ with 4 g/L SLP in 5% ionic solution prior to shaking. 1A shows the treatment vial from below, with the precipitate visible as dark solids settled at the bottom. 1B shows the same treatment vial from the side.
Figure 1B:
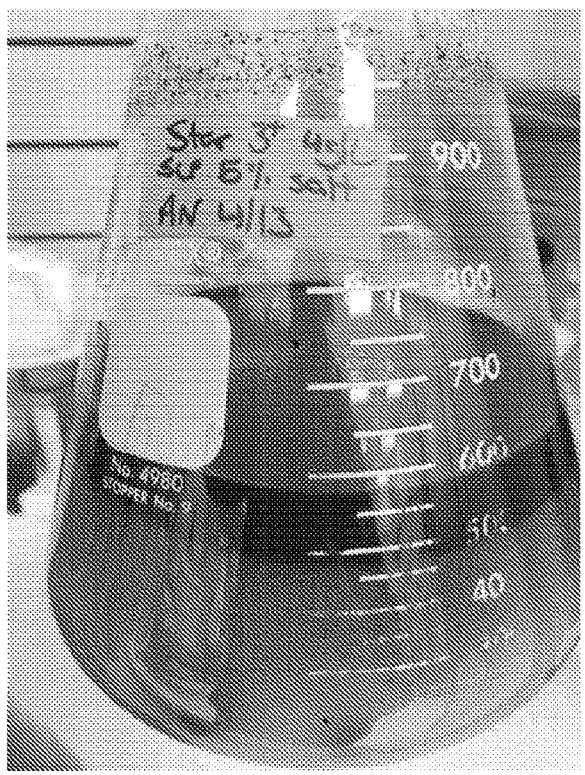
Figure 2A:
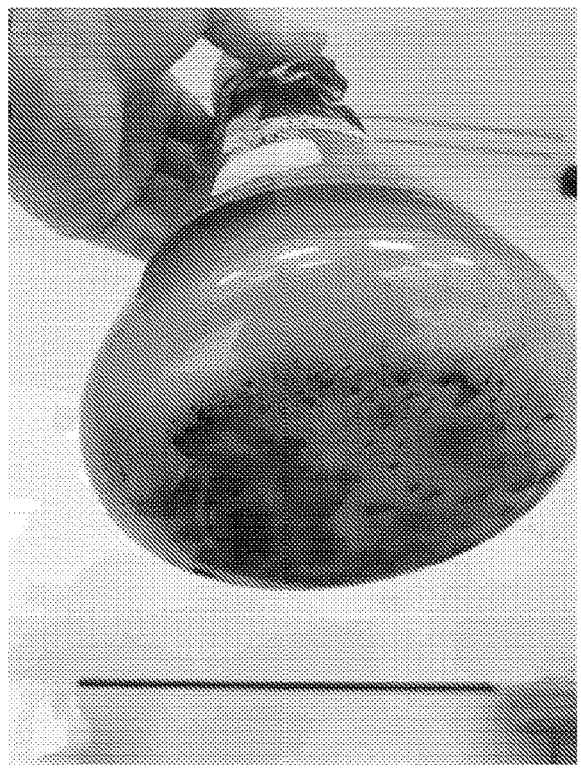
FIGS. 2A-2B show 100 g of asphaltene precipitate in Star 3+ with 4 g/L SLP and 1% ionic solution prior to shaking. 2A shows the treatment vial from below, with the precipitate visible as dark solids settled at the bottom. 2B shows the same treatment vial from the side.
Figure 2B:
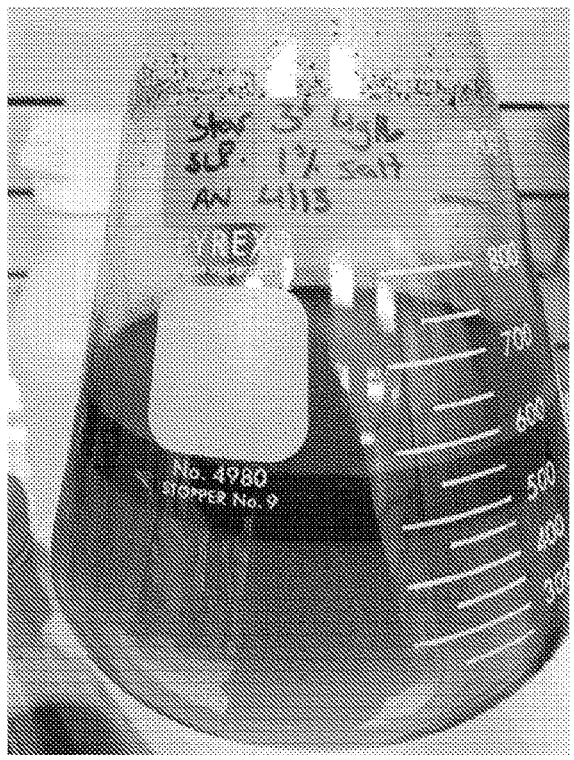
Figure 3A:
FIGS. 3A-3B show 100 g of asphaltene precipitate in Star 3+ with 4 g/L SLP prior to shaking. 3A shows the treatment vial from below, with the precipitate visible as dark solids settled at the bottom. 3B shows the same treatment vial from the side.
Figure 3B:
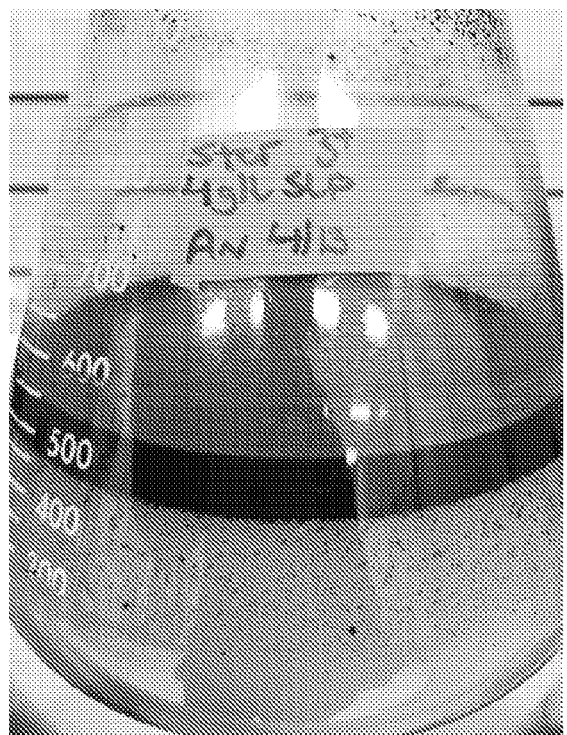
Figure 4A:
FIGS. 4A-4B show 100 g of asphaltene precipitate in Star 3+ treatment alone prior to shaking. 4A shows the treatment vial from below, with the precipitate visible as dark solids settled at the bottom. 4B shows the same treatment vial from the side.
Figure 4B:
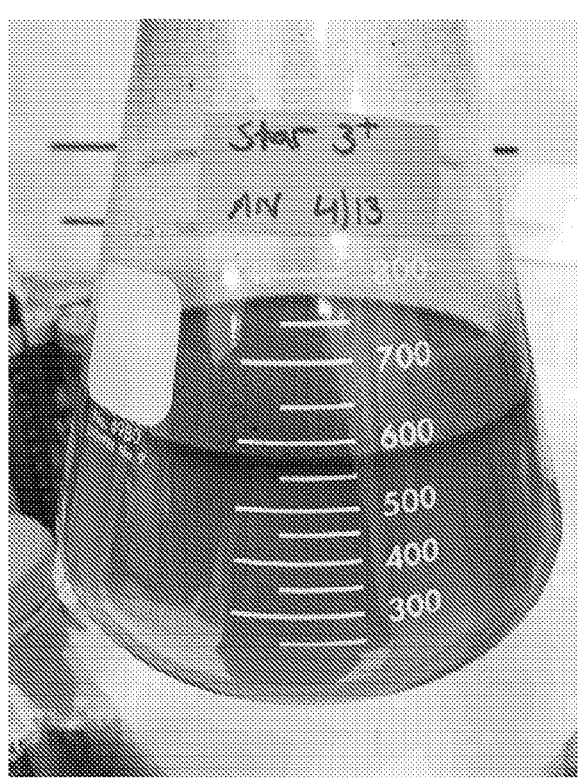
Figure 5A:
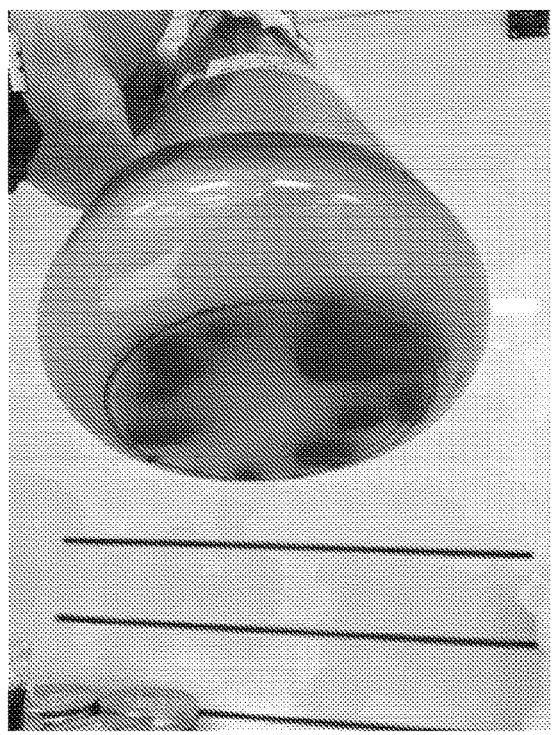
FIGS. 5A-5B show 100 g of asphaltene precipitate in Star 3 treatment alone prior to shaking. 5A shows the treatment vial from below, with the precipitate visible as dark solids settled at the bottom. 5B shows the same treatment vial from the side.
Figure 5B:
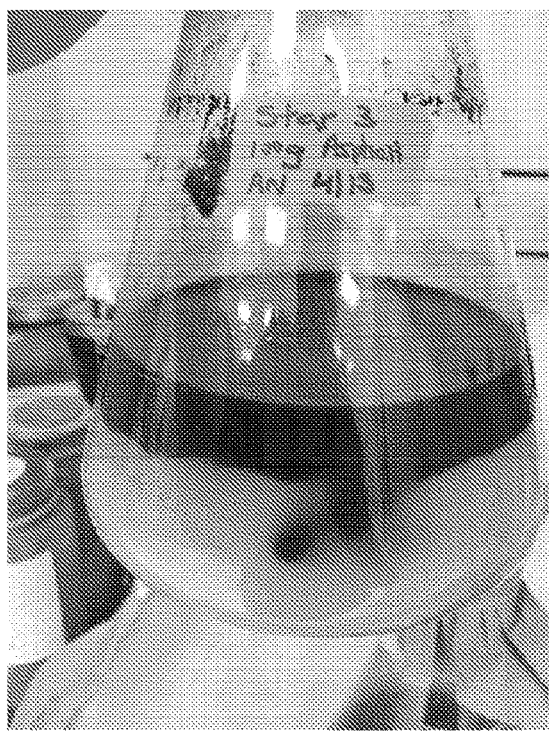
Figure 6:
FIG. 6 shows each of the flasks in FIGS. 1-5, prior to shaking.
Figure 9:
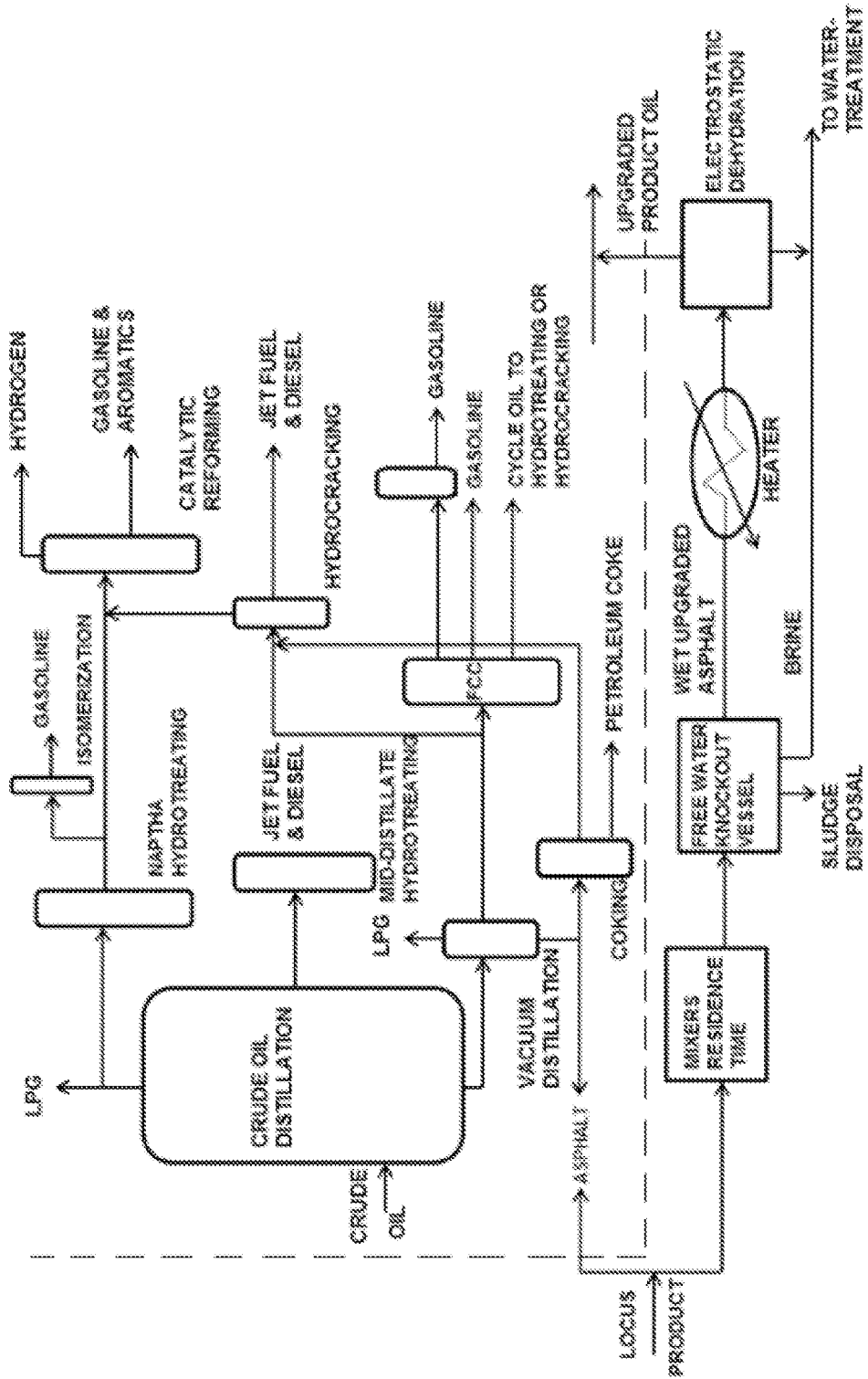
FIG. 9 shows a flow diagram exemplifying application of the subject microbe-based product within the oil refinery process.
Figure 10A:
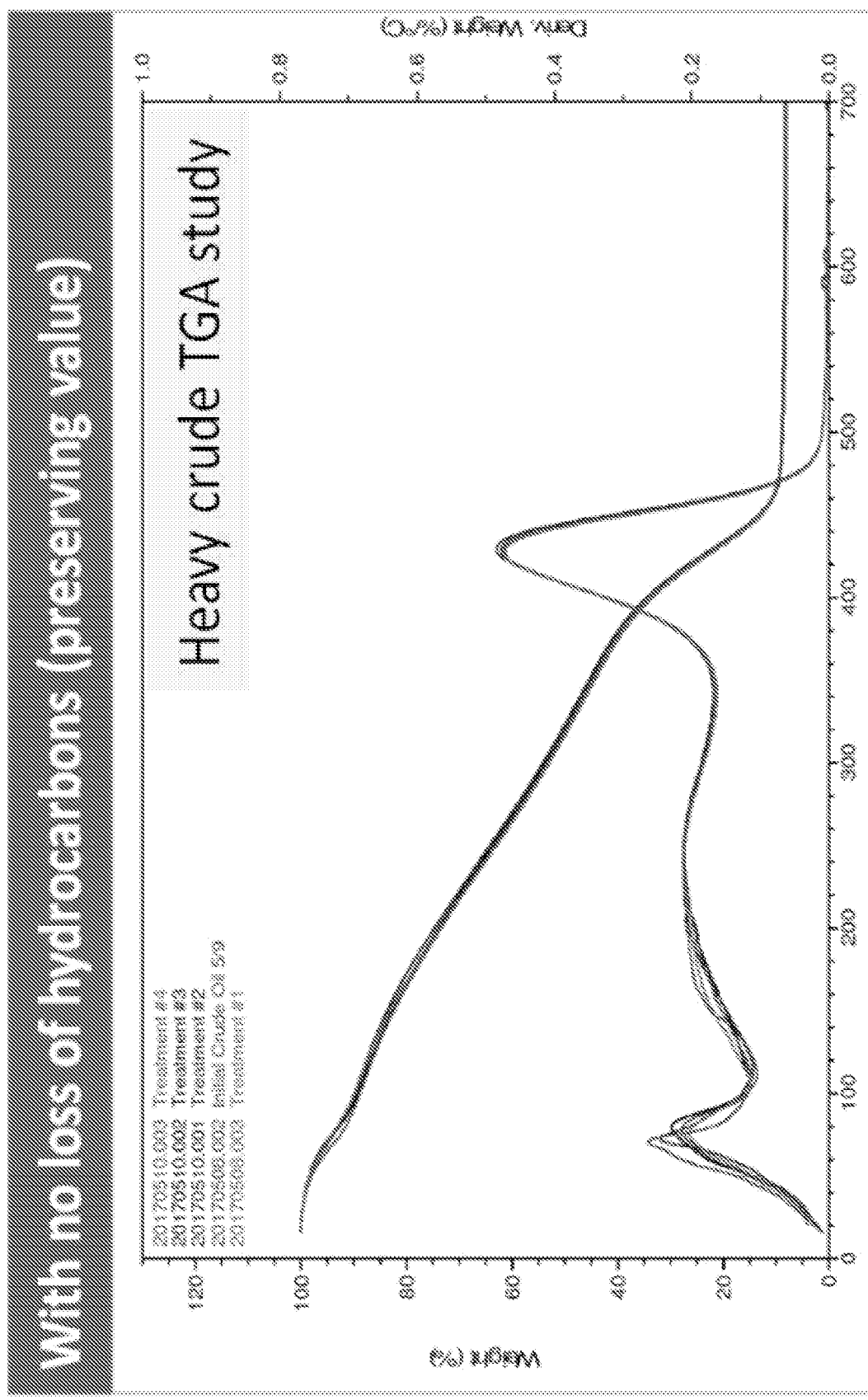
FIGS. 10A-10B show results of a heavy crude TGA study (10A) and BTU increase (10B) after treatment with subject invention.
Figures 10B, 11:
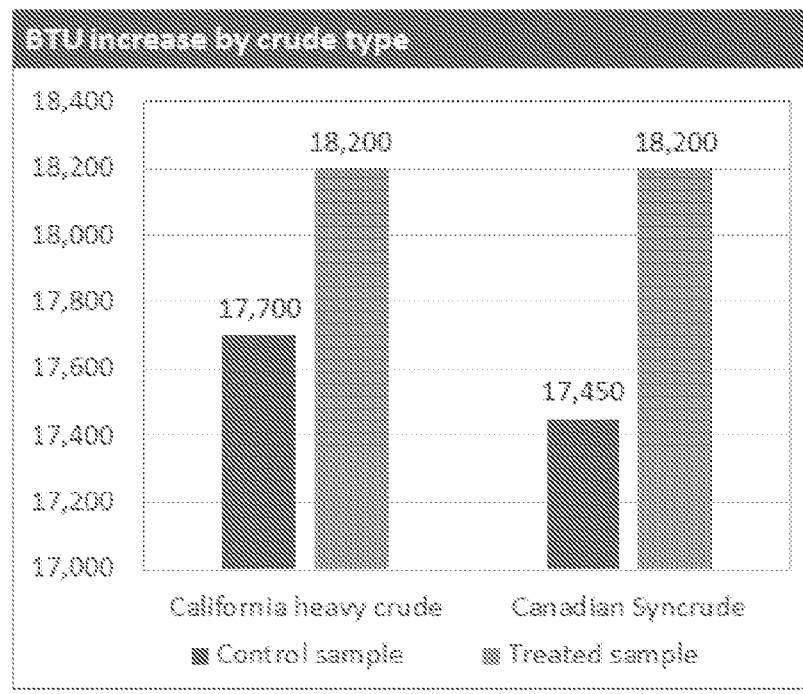
FIG. 11 shows API increase and viscosity reduction after application of the subject treatment to three different types of oil at 80° F.
Figure 12:
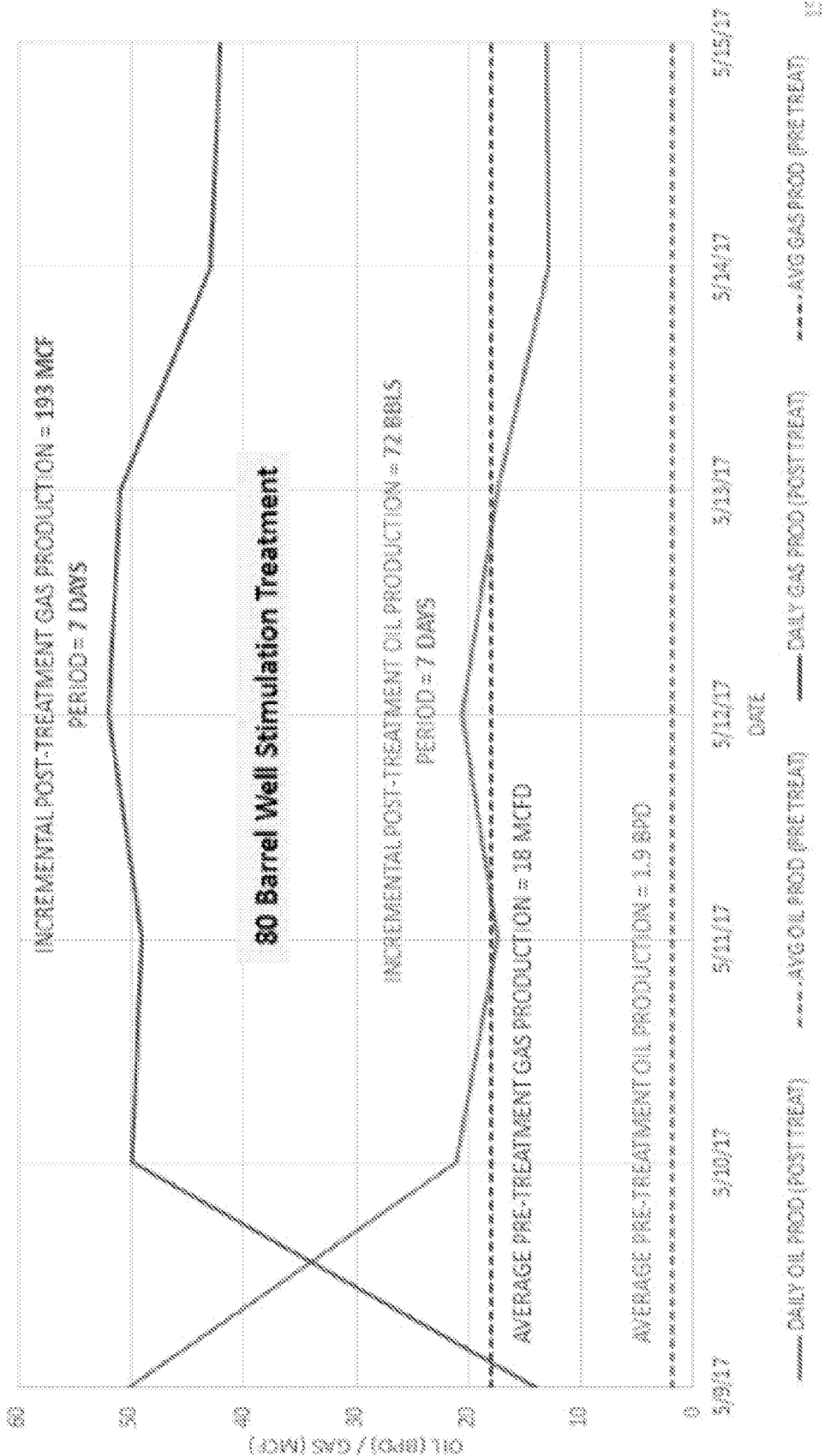
FIG. 12 shows results of paraffin dispersal and well stimulation treatment in a horizontal well (Speechley Sand, PA).
Figure 13:
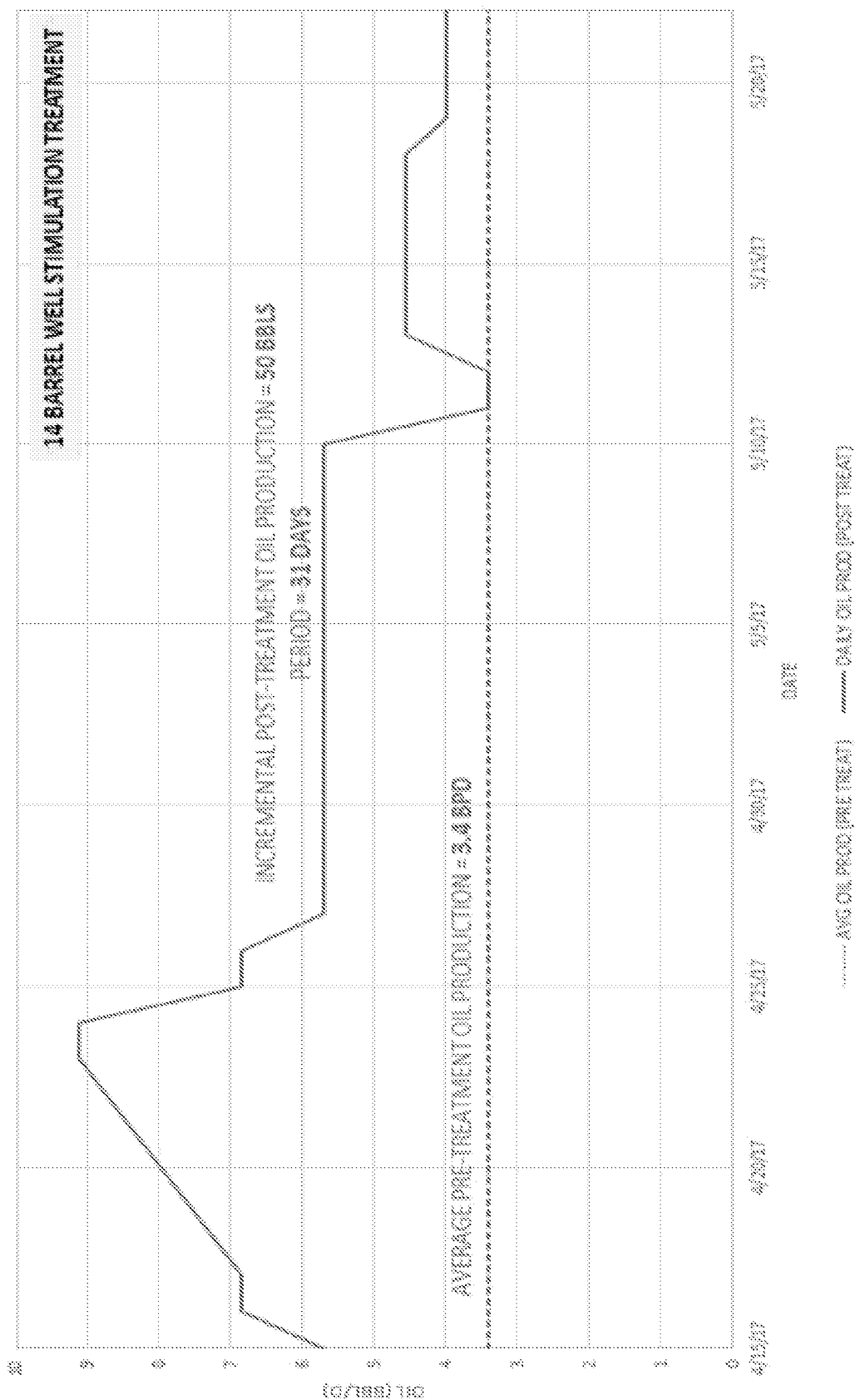
FIG. 13 shows results of paraffin dispersal and well stimulation treatment in a vertical well (Termpeauleau Dolomite, OH).

The subject invention provides advantageous microbe-based products that contain microbes and/or their growth by-products. The by-products of their growth can be, for example, biosurfactants, solvents, and/or enzymes. The subject invention also provides methods of using these microbe-based products. Advantageously, the microbe-based products and methods of the subject invention create a microbial ecosystem, where most, if not all, chemicals are replaced by microbial treatments. Thus, the subject invention is environmentally-friendly, operational-friendly and cost-effective when compared to conventional control treatments.

The subject invention provides compositions and methods for paraffin and/or asphaltene removal utilizing biochemical-producing microbes. The biochemicals produced by the microbes may be, for example, biosurfactants. In additional embodiments, the compositions and methods of the subject invention can liquefy solid paraffin and asphaltene, as well as disperse paraffin and asphaltene that has precipitated from oil.

In one embodiment, the subject invention provides microbe-based products, as well as their use in enhancing oil well performance and removing contaminating compositions such as biofilm, scale, paraffin, and/or asphaltene from oil drilling sites and oil production equipment.

In further embodiments, the materials and methods of the subject invention can be used for bioremediation, including bioremediation of hydrocarbon-contaminated waters, soils, and other sites.

In certain embodiments, the subject invention provides a method for improving oil production efficiency by applying to an oil well a composition having a yeast microbe and/or a growth product thereof. Optionally, the method can further comprise adding nutrients that are beneficial to microbial growth, such as, for example, nitrogen, nitrate, phosphorus, magnesium, carbon, and/or electron-accepting salts. Advantageously, the subject method works to simultaneously stimulate the oil well while removing paraffin, asphaltenes, scale, and/or other contaminants from the well and from oil production equipment.

In certain embodiments, the methods are used for stimulating oil wells, and/or improving enhancing, and/or simultaneously maintaining, for example, pipes, drills, tanks and other structures and equipment involved in oil and/or gas production, transportation, storage and/or refining. The subject invention can also be used in the maintenance and/or stimulation of horizontal, vertical and/or fracking wells, stripper (or marginal) wells, flowlines, and to clean storage tank bottoms.

In certain embodiments, the microbe-based composition of the subject invention comprises microorganisms and biosurfactants. The biosurfactants can be those produced by the microorganisms themselves, or biosurfactants can be added in a crude and/or purified form. In some embodiments, the composition further comprises an ionic or semi-ionic liquid.

In certain embodiments, the biosurfactants work synergistically with other metabolites that are also produced by the microbes.

In certain embodiments, the subject invention provides a method for improving oil production efficiency by applying to an oil well a composition having a yeast microbe and/or a growth product thereof. The composition can further comprise baker's and/or brewer's yeast, yeast extracts, salts, solvents, and biosurfactants.

In further embodiments, a method for biochemically enhanced oil recovery is provided, wherein a composition comprising one or more of each of the following is applied to the well: a biosurfactant, ammonium hydroxide, an ammonium salt and an alcohol solvent. In this method, the composition does not comprise a microorganism, and thus, is particularly useful for improving oil production from stripper wells.

Optionally, the methods can further comprise adding nutrients that are beneficial to microbial growth, such as, for example, nitrogen, nitrate, phosphorus, magnesium, carbon, and/or electron-accepting salts.

The compositions and methods of the subject invention can be used in paraffin and/or asphaltene removal (e.g., from rods, tubing, casing, tanks, pipelines, flow lines, etc.) and emulsification; prevention of corrosion of petroleum production/transmission/refining equipment; reduction of $H_2S$ concentration in wells and extracted crude oil; cleaning of oil field pipe lines, tanks, flow lines, storage tanks and wellbores; scale, sludge, and/or biofilm removal; prevention of scale, sludge, and/or biofilm buildup; dispersion of precipitated paraffin and/or asphaltene; and reduction in viscosity of heavy crude oil.

Figures 14, 15:
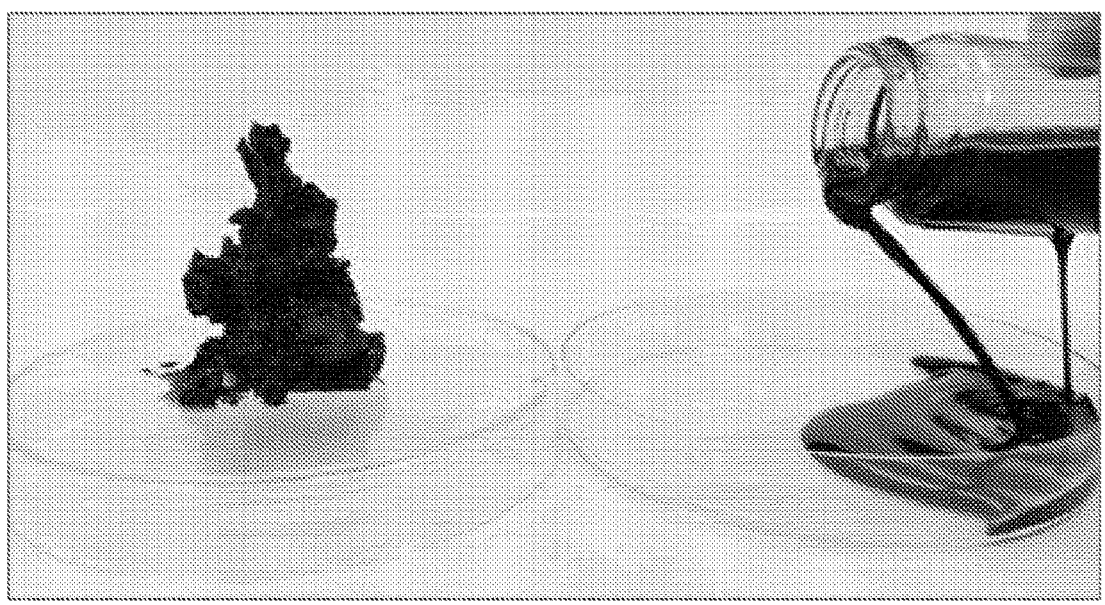
FIG. 14 shows the advantages of the subject invention in paraffin control over hot water, hot oil and solvent-based methods. In particular, traditional methods may temporarily remove paraffin wax but must be repeated often. Furthermore, traditional hot oiling and hot water treatments may damage formations by pushing paraffin further into the formation, and solvents can be extremely toxic.
FIG. 15 shows solid asphaltene (left) and dispersal of solid asphaltene using the subject invention (right).
Figure 16:
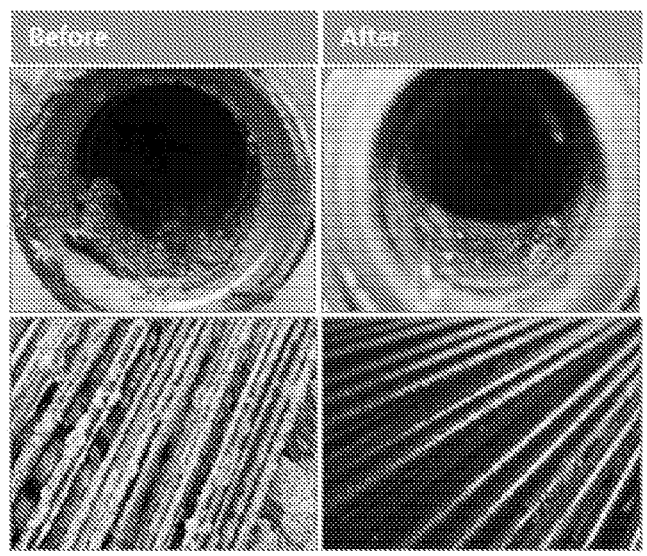
FIG. 16 shows paraffin-contaminated equipment before and after treatment with the subject invention.
Figure 17:
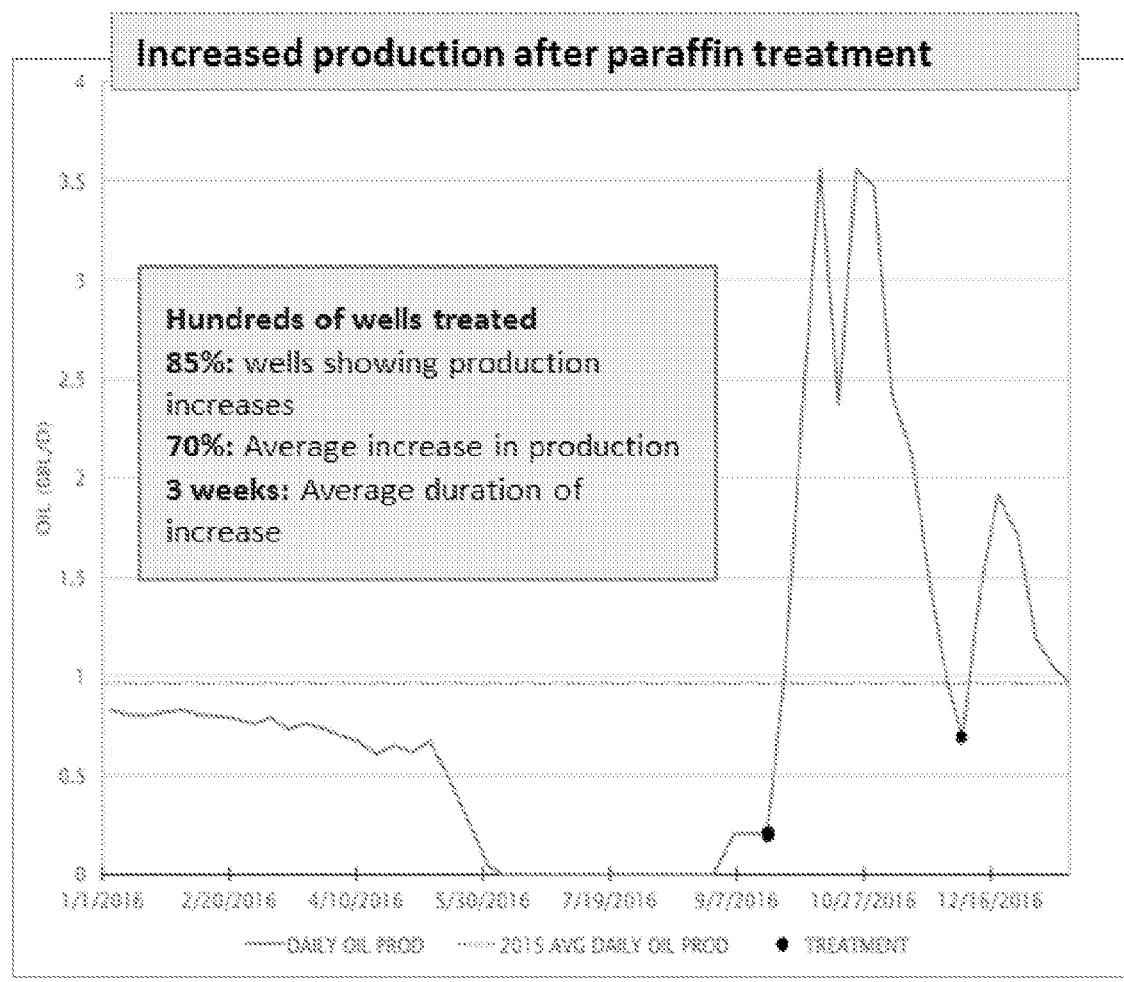
FIG. 17 shows the increase of production in a well before and after treatment with the subject invention.
Figure 18:
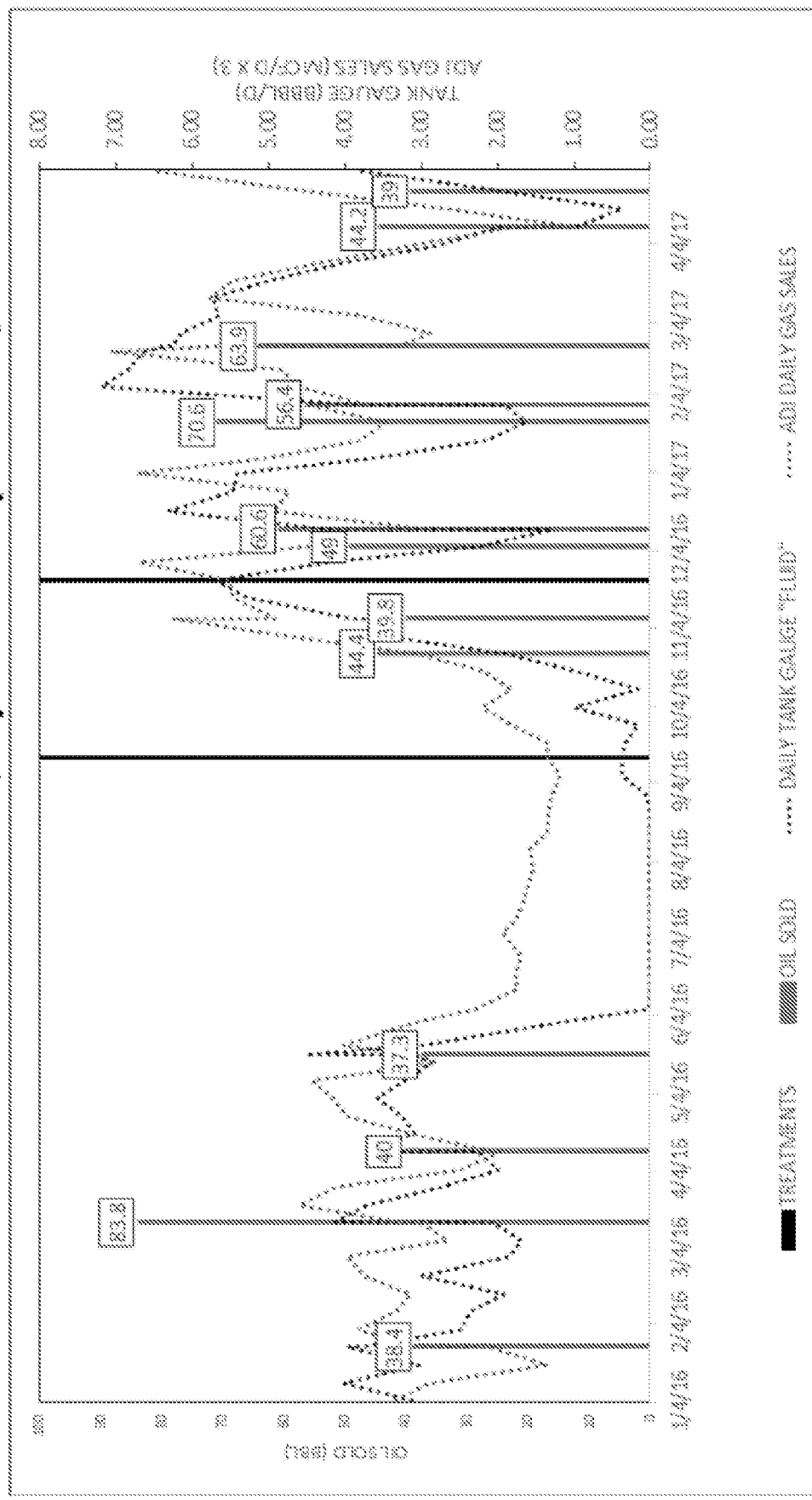
FIG. 18 shows the effects of the subject treatment on oil sold (BBL), tank gauge (BBL/D) and ADJ gas sales (MCF/D×3) before and after treatment of a vertical well (Speechley Sand, PA). The two solid, dark-colored vertical lines depict the points at which treatments was administered to the well. Pre-treatment oil production rate was 0.6 BPD, and post-treatment oil production rate was 2.3 BPD, with a 280% total increase.
Figure 19:
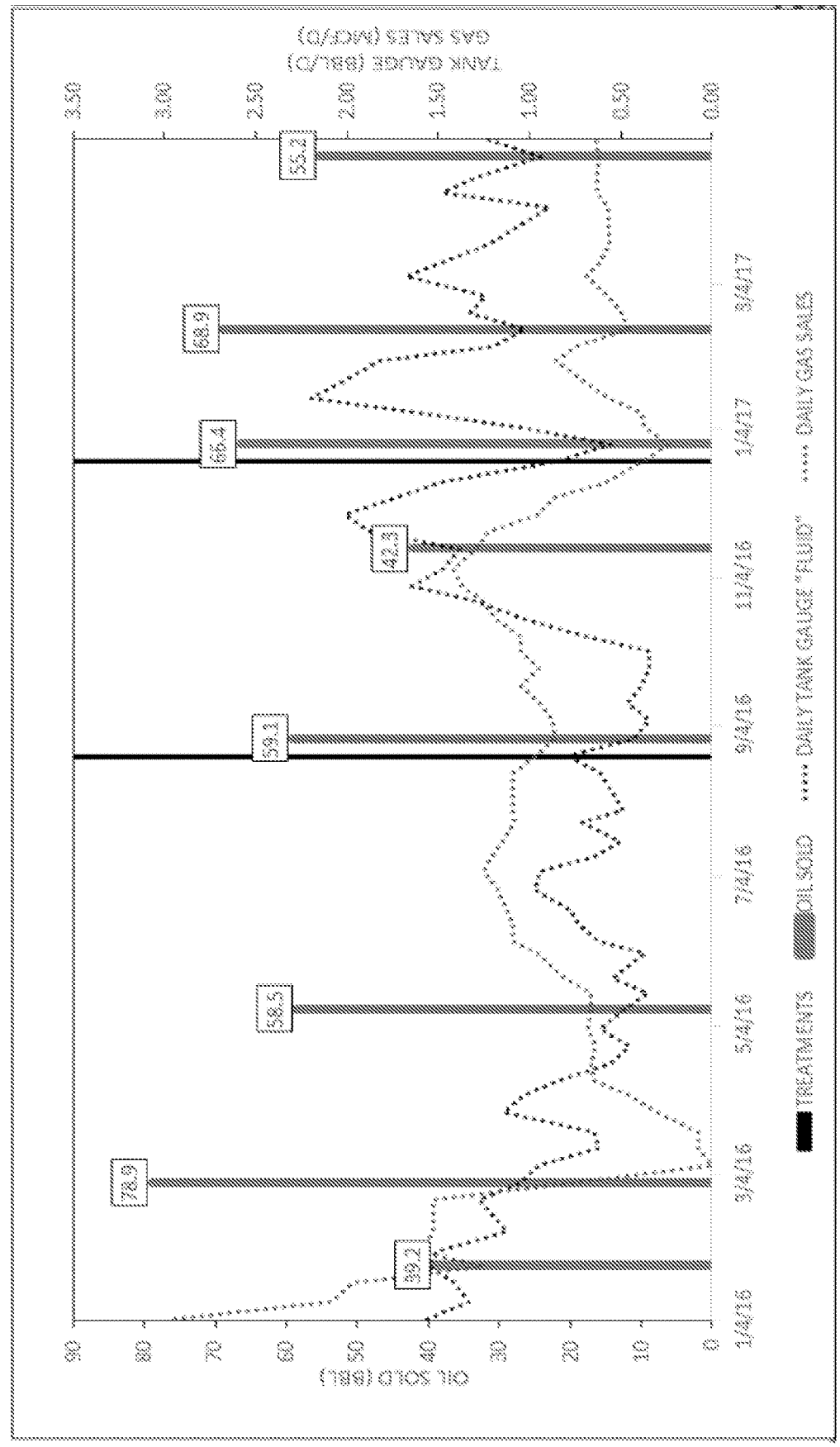
FIG. 19 shows the effects of the subject treatment on oil sold (BBL), tank gauge (BBL/D) and gas sales (MCF/D) before and after treatment of a vertical well (Nineveh Sand, PA). The two solid, dark-colored vertical lines depict the points at which treatments was administered to the well.
Figure 20:
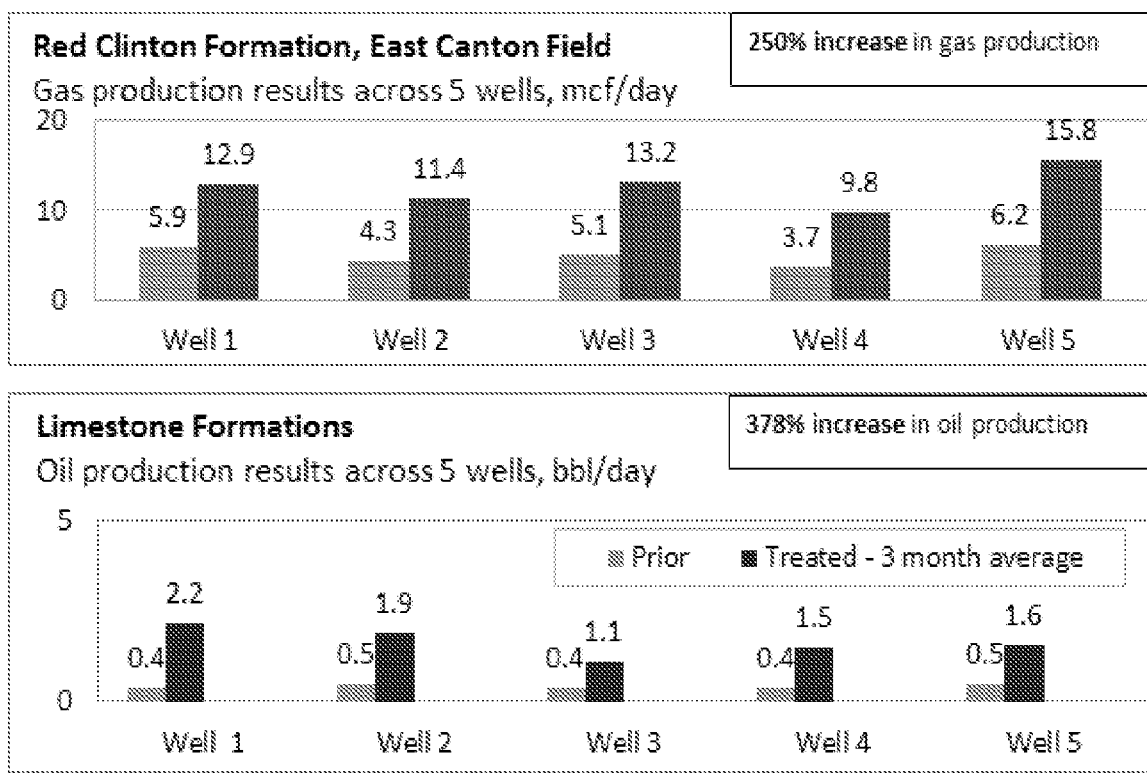
FIG. 20 shows examples of an alternating paraffin dispersal and well stimulation treatment regimen, with formations having temperatures up to 90° C., pH of 2.0, 15 mD and 15% porosity, and up to 15% salinity.

Advantageously, the subject paraffin and asphaltene liquefaction and dispersal treatments can free stuck or floating rods, allowing inoperable wells to resume normal operation. Furthermore, the subject treatments can open up clogged channels, thus allowing for improved oil production. Even further, the subject treatments require lower frequencies of application when compared to hot oil, water or solvents. FIG. 14 shows a comparison of the subject invention with conventional methods.

In one embodiment, a composition of the subject invention can efficiently liquefy solid paraffin at, for example, 25 to 60° C. In some embodiments, the subject invention can also efficiently liquefy asphaltenes, asphalts, and resins into more valuable and useful components, such as distillates and/or gas oil fractions, without degrading the crude oil into methane or other gases. This can be achieved, for example, overnight (or, in 12 hours or less). The asphaltenes and resins can, for example, be upgraded into a flammable, soluble form, with advantages over their less flammable solid states. Advantageously, the subject compositions and methods operate without causing an increase in TAN (total acid number) of oil.

The application of the microbe-based products of the present invention can be performed during drilling operations (e.g., while drilling, while tripping-in or tripping-out of the hole, while circulating mud, while casing, while placing a production liner, and/or while cementing, etc.), and as a production treatment. Advantageously, the microbe-based products do not form biofilms within oil and gas producing formations and equipment.

In some embodiments, the method utilizes yeast strains and/or by-products of their growth. In one embodiment, the microbe used in the methods of the subject invention is a biosurfactant-producing yeast. The invention provides, for example, a microbe-based product comprising cultivated *Starmerella bombicola* ATCC 22214 and/or products of the growth of that microbe. In addition, the invention provides a microbe-based product comprising cultivated killer yeast strains such as, for example, *Wickerhamomyces anomalus* yeast and/or its growth byproducts.

In one embodiment, this invention provides a yeast fermentation product designated as "Star 3" that can be used to liquefy precipitated and hardened asphaltene and resin waste. The Star 3 was obtained via cultivation of the sophorolipid-producing yeast, *Starmerella bombicola* ATCC 22214. The fermentation broth after 4 days of cultivation at 30° C. contained the yeast cell suspension and 4 g/L sophorolipid.

In one embodiment, this invention provides a yeast fermentation product designated as "Star 3+" that can be used to liquefy precipitated and hardened asphaltene and resin waste. The Star 3+ was obtained via cultivation of the sophorolipid-producing killer yeast, *Wickerhamomyces anomalus* (*Pichia anomala*) in medium containing necessary sources of carbon, nitrogen, minerals and optionally, antimicrobial substances to prevent contaminating bacterial growth. The culture can be grown with an additional carbon source, particularly, a saturated oil. The fermentation broth was harvested after 48-72 hours of cultivation at 25-30° C. and pH of about 5.0 to about 5.5. This is the Star 3+ product.

In one embodiment the subject invention provides a method for improving oil production efficiency by applying to an oil well a composition having a *Starmerella* yeast microbe and/or a growth product thereof. In certain embodiments, the composition comprises Star 3.

In one embodiment the subject invention provides a method for improving oil production efficiency by applying to an oil well a composition having a killer yeast microbe (e.g., *Pichia anomala*) and/or a growth product thereof. In certain preferred embodiments, the composition comprises Star 3+.

In one embodiment, the microbe-based combinations according to the subject invention are obtained through cultivation processes ranging from small to large scale. The cultivation process can be, for example, submerged cultivation, surface cultivation, solid state fermentation (SSF), and/or a combination thereof.

Selected Definitions

As used herein, "contaminant" refers to any substance that causes another substance or object to become fouled or impure. Contaminants can be living or non-living and can be inorganic or organic substances or deposits. Furthermore, contaminants can include, but are not limited to, hydrocarbons, such as petroleum, tar sands or asphaltenes; fats, oils and greases (FOG), such as cooking grease and lard; lipids; waxes, such as paraffin; resins; biofilms; or any other substances referred to as, for example, dirt, dust, scale (including iron sulfide scale), sludge, crud, slag, grime, scum, plaque, buildup, or residue.

As used herein, "cleaning" as used in the context of contaminants or fouling means removal or reduction of contaminants from a surface or a piece of equipment. Cleaning can include purifying, defouling, decontaminating, clearing or unclogging, and can be achieved by any means, including but not limited to, melting, dispersing, emulsifying, dissolving, scraping, degrading, blasting, soaking, or cleaving the contaminant. Cleaning can further include controlling, inhibiting or preventing further fouling or contamination from occurring.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with broth in which they were grown, in the microbe-based composition. The microbes may be present at, for example, a concentration of $1\times10^4$, $1\times10^5$, $1\times10^6$, $1\times10^7$, $1\times10^8$, $1\times10^9$, $1\times10^{10}$, or $1\times10^{11}$ or more propagules per milliliter of the composition. As used herein, a propagule is any portion of a microorganism from which a new and/or mature organism can develop, including but not limited to, cells, spores, mycelia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, an "isolated" or "purified" nucleic acid molecule, polynucleotide, polypeptide, protein or organic compound, such as a small molecule, is substantially free of other compounds, such as cellular material, with which it is associated in nature. As used herein, reference to an "isolated" strain means that the strain is removed from the environment in which it exists in nature. Thus, the isolated strain may exist as, for example, a biologically pure culture, or as spores (or other forms of the strain) in association with an agricultural carrier.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of other molecules, or the amino acids that flank it, in its naturally-occurring state.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19 and 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduces" means a negative alteration of at least 1%, 5%, 10%, 25%, 50%, 75%, or 100%.

As used herein, "reference" means a standard or control condition.

As used herein, "salt-tolerant" in the context of a microbe means the microbe is capable of growing in a sodium chloride concentration of 15% or greater. In a specific embodiment, "salt-tolerant" refers to the ability to grow in 150 g/L or more of NaCl.

A "metabolite" refers to any substance produced by metabolism (i.e., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, enzymes, toxins, acids, solvents, gasses, alcohols, proteins, vitamins, minerals, microelements, amino acids, polymers, and surfactants.

As used herein, "surfactant" means a compound that lowers the surface tension (or interfacial tension) between two liquids or between a liquid and a solid. Surfactants act as detergents, wetting agents, emulsifiers, foaming agents, and/or dispersants. A "biosurfactant" is a surface-active substance produced by a living cell.

As used herein, "heavy oil" or "heavy hydrocarbons" mean viscous hydrocarbon fluids. Heavy hydrocarbons may include highly viscous hydrocarbon fluids such as heavy oil, extra heavy oil, tar, and/or asphalt. Heavy and extra heavy oils are highly viscous with a density close to or even exceeding water. Heavy hydrocarbons may comprise moderate to high quantities of paraffins, resins and asphaltenes, as well as smaller concentrations of sulfur, oxygen, and nitrogen. Heavy hydrocarbons may also include aromatics or other complex ring hydrocarbons. Additional elements may also be present in heavy hydrocarbons in trace amounts. Heavy hydrocarbons may be classified by API gravity. Heavy hydrocarbons generally have an API gravity below about 20°. Heavy oil, for example, generally has an API gravity of about 10-20°, whereas extra heavy oil generally has an API gravity below about 12°. The viscosity of heavy hydrocarbons is generally greater than about 200 cp at reservoir conditions, and that of extra heavy oil is generally about 10,000 cp or more.

Growth of Microbes According to the Subject Invention

The subject invention provides methods for cultivation of microorganisms and production of microbial metabolites and/or other by-products of microbial growth. The microbial cultivation systems would typically use submerged culture fermentation; however, surface culture and hybrid systems can also be used. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

In one embodiment, the subject invention provides methods of producing a microbial metabolite by cultivating a microbe strain of the subject invention under conditions appropriate for growth and production of the metabolite; and purifying the metabolite. In a specific embodiment, the metabolite is a biosurfactant.

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, isopropyl, propanol, butanol, pentanol, hexanol, isobutanol, and/or glycerol; fats and oils such as soybean oil, rice bran oil, canola oil, olive oil, corn oil, sesame oil, and/or linseed oil; etc. These carbon sources may be used independently or in a combination of two or more.

In a preferred embodiment, the method comprises use of two carbon sources, one of which is a saturated oil selected from canola, vegetable, corn, coconut, olive, or any other oil suitable for use in, for example, cooking. In a specific embodiment, the saturated oil is 2% canola oil.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the foam of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included, e.g., L-Alanine.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium chloride and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention further provides a method for producing microbial metabolites such as ethanol, lactic acid, beta-glucan, proteins, peptides, metabolic intermediates, polyunsaturated fatty acid, and lipids. The metabolite content produced by the method can be, for example, at least 20%, 30%, 40%, 50%, 60%, 70%, 80%, or 90%.

The biomass content of the fermentation broth may be, for example from 5 g/l to 180 g/l or more. In one embodiment, the solids content of the broth is from 10 g/l to 150 g/l.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a microbe-free broth or contain cells, spores, mycelia, conidia or other reproductive propagules v. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

Advantageously, the microbe-based products can be produced in remote locations. In one embodiment, the microbe-based products can be used for human nutrition and/or disease prevention and/or treatment. The microbe growth facilities may operate off the grid by utilizing, for example, solar, wind and/or hydroelectric power.

Microbial Strains Grown in Accordance with the Subject Invention

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. Procedures for making mutants are well known in the microbiological art. For example, ultraviolet light and nitrosoguanidine are used extensively toward this end.

In one embodiment, the microorganism is a yeast or fungus. Yeast and fungus species suitable for use according to the current invention, include *Candida*, *Saccharomyces* (*S. cerevisiae*, *S. boulardii sequela*, *S. torula*), *Issalchenkia*, *Kluyveromyces*, *Pichia*, *Wickerhamomyces* (e.g., *W. anomalus*), *Starmerella* (e.g., *S. bombicola*), *Mycorrhiza*, *Mortierella*, *Phycomyces*, *Blakeslea*, *Thraustochytrium*, *Phythium*, *Entomophthora*, *Aureobasidium pullulans*, *Pseudozyma aphidis*, *Fusarium venenalum*, *Aspergillus*, *Trichoderma* (e.g., *T. reesei*, *T. harzianum*, *T. hamatum*, *T. viride*), and/or *Rhizopus* spp.

In one embodiment, the yeast is a killer yeast. As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. For example, microorganisms that can be controlled by killer yeast include *Fusarium* and other filamentous fungi. Examples of killer yeasts according to the present invention are those that can be used safely in the food and fermentation industries, e.g., beer, wine, and bread making; those that can be used to control other microorganisms that might contaminate such production processes; those that can be used in biocontrol for food preservation; those than can be used for treatment of fungal infections in both humans and plants; and those that can be used in recombinant DNA technology. Such yeasts can include, but are not limited to, *Wickerhamomyces*, *Pichia* (e.g., *P. anomala*, *P. guiellier-mondii*, *P. kudriavzevii*), *Hansenula*, *Saccharomyces*, *Hanseniaspora*, (e.g., *H. uvarum*), *Ustilago maydis*, *Debaryomyces hansenii*, *Candida*, *Cryptococcus*, *Kluyveromyces*, *Torulopsis*, *Ustilago*, *Williopsis*, *Zygosaccharomyces* (e.g., *Z. bailii*), and others.

In preferred embodiments, the microbes may be chosen from strains of killer yeast. In even more preferred embodiments, the microbes are *Wickerhamomyces anomalus* strains.

*Wickerhamomyces anomalus*, also known as *Pichia anomala* and *Hansenula anomala*, is frequently associated with food and grain production. *W. anomalus* produces a killer toxin comprising exo-$\beta$-1,3-glucanase. Additionally, *W. anomalus* produces biosurfactants that are capable of reducing surface/interfacial tension of water, as well as various other useful solvents, enzymes and metabolites, such as phytase, ethyl acetate, acetic acid, lactic acid, isopropyl alcohol, ethanol, and others.

In one embodiment, the microbial strain is chosen from the *Starmerella* clade. A culture of a *Starmerella* microbe useful according to the subject invention, *Starmerella bombicola*, can be obtained from the American Type Culture Collection (ATCC), 10801 University Blvd., Manassas, Va. 20110-2209 USA. The deposit has been assigned accession number ATCC No. 22214 by the depository.

In one embodiment, the subject invention provides the use of yeast strain ATCC 22214 and mutants thereof. This strain is an effective producer of sophorolipid (SLP) biosurfactants.

In one embodiment, the microbe is a strain of *Pseudozyma aphidis*. This microbe is an effective producer of mannosylerythritol lipid (MEL) biosurfactants.

In some embodiments, the microorganisms are bacteria, including gram-positive and gram-negative bacteria. The bacteria may be, for example *Bacillus* (e.g., *B. subtilis, B. licheniformis, B. firmus, B. laterosporus, B. megaterium, B. amyloliquifaciens*), *Clostridium* (*C. butyricum, C. tyrobutyricum, C. acetobutyricum, Clostridium* NIPER 7, and *C. beijerinckii*), *Azobacter* (*A. vinelandii, A. chroococcum*), *Pseudomonas* (*P. chlororaphis* subsp. *aureofaciens* (*Kluyver*), *P. aeruginosa*), *Agrobacterium radiobacter, Azospirillum brasiliensis, Rhizobium, Sphingomonas paucimobilis, Ralslonia eulropha*, and/or *Rhodospirillum rubrum*.

In one embodiment, the microbe is a non-pathogenic strain of *Pseudomonas*. Preferably, the strain is a producer of rhamnolipid (RLP) biosurfactants.

In one embodiment, the microbe is a strain of *Bacillus subtilis*, which is an effective producer of surfactin biosurfactants.

Other microbial strains including, for example, other fungal strains capable of accumulating significant amounts of, for example, glycolipid-biosurfactants can be used in accordance with the subject invention. Biosurfactants useful according to the present invention include mannoprotein, beta-glucan and other metabolites that have bio-emulsifying and surface/interfacial tension-reducing properties.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microorganisms in the microbe-based product may be in an active or inactive form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

In certain embodiments, the compositions of the subject invention have advantages over, for example, biosurfactants alone, including one or more of the following: high concentrations of mannoprotein as a part of yeast cell wall's outer surface (mannoprotein is a highly effective bioemulsifier capable of reaching up to an 80% emulsification index); the presence of biopolymer beta-glucan (an emulsifier) in yeast cell walls; the presence of biosurfactants in the culture, which are capable of reducing both surface and interfacial tension; and the presence of metabolites (e.g., lactic acid, ethanol, etc.).

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Examples of such additives include surfactants, emulsifying agents, lubricants, buffering agents, solubility controlling agents, pH adjusting agents, preservatives, stabilizers and ultra-violet light resistant agents.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt as polyprotic acid such as sodium bicarbonate or carbonate, sodium sulfate, sodium phosphate, sodium biphosphate, can be included in the formulation.

In some embodiments, additional components can be added to increase the effectiveness of the microbe-based composition and its use in hydrocarbon treatment, for example by enabling greater extraction of light hydrocarbon fractions, such as light oil and/or tar fractions from asphalt.

For example, in one embodiment, the composition can comprise added purified biosurfactants or solvents in addition to those already present in the composition due to microbial metabolism. In one embodiment, ionic or semi-ionic liquids can be added to the composition to increase its effectiveness. For example, 1%, 2%, 3%, 4%, 5% or greater ionic liquid can be added to the composition. Ionic liquids can act as co-solvents and can prevent the formation of ring bonds in hydrocarbon compositions, which is one cause of hydrocarbon precipitation.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

In one embodiment, this invention provides a yeast fermentation product designated as "Star 3" that can be used to liquefy, for example, precipitated and hardened paraffin, asphaltene and resin waste. The Star 3 was obtained via cultivation of the sophorolipid-producing yeast, *Starmerella bombicola* ATCC 22214. The fermentation broth after 4 days of cultivation at 30° C. contained the yeast cell suspension and 4 g/L sophorolipid.

In one embodiment the subject invention provides a method for improving oil production efficiency by applying to an oil well a composition having a *Starmerella* yeast microbe and/or a growth product thereof. In certain embodiments, the composition comprises Star 3.

In one embodiment, this invention provides a yeast fermentation product designated as "Star 3+" that can be used to liquefy precipitated and hardened asphaltene and resin waste while simultaneously enhancing oil recovery from an oil well. The Star 3+ was obtained via cultivation of the killer yeast, *Wickerhamomyces anomalus* in medium containing necessary sources of carbon, nitrogen, minerals and optionally, antimicrobial substances to prevent contaminating bacterial growth. The culture can be grown with an additional carbon source, particularly, a saturated oil. The fermentation broth was harvested after 48-72 hours of cultivation at 25-30° C. and pH of about 5.0 to about 5.5.

Advantageously, Star 3 and Star 3+ do not form biofilms inside oil and gas producing formations and/or equipment.

Advantageously, the subject compositions can be used to simultaneously enhance oil recovery (e.g., by stimulating an oil well), while removing paraffin, asphaltenes, scale, biofilm and other contaminants from oil production equipment.

In one embodiment the subject invention provides a method for improving oil production efficiency by applying to an oil well a composition having a killer yeast microbe and/or a growth product thereof. In certain embodiments, the composition comprises Star 3+.

In certain preferred embodiments, the composition comprises Star 3+, baker's yeast and/or brewer's yeast (i.e., one or more strains of *Saccharomyces cerevisiae*), yeast extract, salts, solvents and biosurfactants.

Biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes. In one embodiment, the microbial biosurfactant is a glycolipid such as rhamnolipids (RLP), sophorolipids (SLP), trehalose lipid or mannosylerythritol lipid (MEL).

The biosurfactants can be added in purified form or can be present in the microbe-based composition as a result of microbial growth.

Preferably, the biosurfactant is a sophorolipid at a concentration of about 1 g/L to 10 g/L, preferably from about 2 to 5 g/L.

In some embodiments, the biosurfactant can also be a lipopeptide, such as surfactin, and/or a rhamnolipid. Surfactin can be added at a concentration of no greater than 0.05 g/L. Rhamnolipid can be added at a concentration of no greater than 0.05 g/L.

In some embodiments, a blend of biosurfactants is present. Preferably the blend comprises sophorolipids, and optionally one or both of a mannosylerythritol lipid, a surfactin or a rhamnolipid.

In some embodiments, one of the solvents used in the composition is selected from mineral or organic spirits, including, for example, ethanol, butanol, propanol, and isopropyl alcohol. In a preferred embodiment, isopropyl alcohol in an amount of 1 to 100 ml/L, more preferably from 2 to 50 ml/L, is added as to the composition.

In some embodiments, the composition further comprises an ionic or semi-ionic liquid as a solvent. Ionic liquids can act as co-solvents and can prevent the formation of ring bonds in hydrocarbon compositions, which is one cause of hydrocarbon precipitation. Exemplary ionic liquids suitable for the subject composition include, but are not limited to, ethyl ammonium nitrate or glycerin/magnesium sulfate heptahydrate. Preferably, the concentration of ionic liquid in the composition ranges from about 0.1% to about 5%.

Ionic liquids are composed entirely of ions or a combination of cations and anions. Many ionic liquids are in the form of organic salts with melting points below 100° C., or often even lower than room temperature. The most common ionic liquids are those prepared from organic-based cations and inorganic or organic anions. At least one ion has a delocalized charge and one component is organic, which prevents the formation of a stable crystal lattice. Ionic liquids may be suitable, for example, for use as catalysts and solvents in alkylation and polymerization reactions, as well as in dimerization, oligomerization acetylation, metatheses and copolymerization reactions. Properties of ionic liquids, such as melting point, viscosity and solubility are determined by the substituents on the organic component and by the counter-ion.

In some embodiments, the composition further comprises ammonium hydroxide as a solvent. Preferably, the ammonium hydroxide (70% solution) is present in the composition at a concentration of about 1 to 50 ml/L, more preferably from 3 to 10 ml/L.

In some embodiments, the composition further comprises salts and/or mineral salts selected from phosphorous, magnesium, potassium, glucose and ammonium. Preferably, from 1 to 20 g/L, and more preferably from 2 to 10 g/L of ammonium salt is added, for example, ammonium phosphate, diammonium phosphate, ammonium chloride, or another dibasic or monobasic salt.

In some embodiments, the composition further comprises yeast extract at a concentration of 1 to 50 g/L, preferably from 1 to 20 g/L.

In some embodiments wherein there is a high presence of wax and scale, for example, the composition can comprise baker's and/or brewer's yeast (i.e., a strain of *Saccharomyces cerevisiae*). Preferably, the concentration of *Saccharomyces* yeast present in the composition is from 0% to 1%.

In one embodiment, this invention provides a biochemical product for enhanced oil recovery. The product for biochemically enhanced oil recovery can comprise one or more of each of the following: one or more biosurfactants, ammonium hydroxide, an ammonium salt, and an alcohol solvent, but does not comprise microorganisms. This is particularly useful for enhancing oil recovery from stripper wells.

The blend of biosurfactants used in the product for biochemically enhanced oil recovery can be formulated using any number of combinations and proportions. In certain embodiments, the composition comprises SLP, MEL, RLP and/or surfactin.

In certain embodiments, the biosurfactant blend comprises only SLP at a concentration of about 2 ml (of 400-500 g/L solution) per liter of composition.

In some embodiments, the composition for biochemically enhanced oil recovery comprises a solvent. The solvent can be an alcohol, for example, ethanol or isopropyl alcohol. In specific embodiments, the solvent is isopropyl alcohol at a concentration of 1 ml/L to 5 ml/L, preferably a concentration of about 3 ml/L. In certain embodiments, the solvent is added in a concentration of 25 to 100 g/L, preferably 30 to 35 g/L.

In some embodiments, the ammonium salt can be ammonium chloride, ammonium phosphate, or diammonium phosphate. In specific embodiments, the ammonium salt is ammonium phosphate or diammonium phosphate at a concentration of 1 to 5 ml/L, preferably about 2 ml/L. In certain embodiments, the ammonium salt is added in a concentration of 2 to 10 g/L.

In some embodiments, the composition for biochemically enhanced oil recovery comprises ammonium hydroxide. In specific embodiments, the concentration of ammonium hydroxide is from 1 ml/L to 10 ml/L, preferably about 3 ml/L, In some embodiments, the ammonium hydroxide is a 70% solution.

In an exemplary embodiment, the microbe-based product is formulated by adding 100 gallons of the culture medium comprising the microorganism and its growth by-products, with 100 gallons of a solution of water and biosurfactants. The biosurfactants, preferably sophorolipids, are present in the final composition at a concentration of 0.005 to 0.1 g/L. Isopropyl alcohol (2-50 mL/L) and diammonium phosphate or ammonium phosphate (2-5 g/L) can also be added to the product.

Removal of Contaminants while Enhancing Oil Recovery

The subject invention provides materials and methods for improving oil production from an oil drilling site. Advantageously, the subject invention utilizes one treatment to perform two simultaneous mechanisms of improving oil recovery. In particular, the subject invention can be used to enhance oil recovery by, for example, stimulating oil flow from a well, while removing paraffins, asphaltenes, scales and other contaminants from oil wells and oil production equipment that might, for example, obstruct or slow the flow of oil. This invention is particularly useful in vertical wells and can also be used to enhance oil recovery from stripper (or under-producing) wells.

In one aspect, the subject invention provides methods, systems, and devices for applying the microbe-based products to remove paraffin, asphaltene and other contaminating substances from, for example, tubes, pipes, wells, bores, tanks, pumps, and other equipment and material. In another aspect, the subject invention provides methods and materials for treating oil that contains such contaminants. Advantageously, use of the subject invention can improve and/or enhance oil well production, aid in oil well stimulation, as well as restore the health of under-producing or even dead wells.

The subject invention is environmentally friendly in that it can substantially reduce greenhouse gas emissions related to production of heavy crude oil, for example, by 50%, when compared to existing operations. This is mainly due to a reduction in the need for transportation and hauling via fuel-burning trucks, but also due to a reduction in methane released by treatment of the oil, and exhaust from engines, turbines, and fired heaters in the extraction and refining needed for heavy oils.

In specific embodiments, methods are provided for simultaneously enhancing oil recovery from an oil well while removing contaminants from oil and/or gas production or processing equipment, wherein the methods comprise applying a composition of the subject invention to the well and/or equipment. The method can further comprise applying nutrients for microbial growth.

In one embodiment, the method can further comprise applying sophorolipid (0.005-0.1 g/L), ammonium phosphate or diammonium phosphate (2-5 g/L), and isopropyl alcohol (2-50 ml/L) to the well.

As used herein, "applying" a composition or product refers to contacting it with a target or site such that the composition or product can have an effect on that target or site. The effect can be due to, for example, microbial growth and/or the action of a biosurfactant, solvent and/or other growth by-product. Compositions according to the subject invention can be used for cleaning pipes, tanks, tubes, rods, pumps, equipment, soil, and/or surfaces or materials. For example, the microbe-based products can also be injected into oil wells and/or the piping, pumps, tanks, etc. associated with oil wells.

There are many types of contaminants associated with oil processing equipment, such as oils, paraffins, asphalts/asphaltenes, resins, sulfur, tar by-products, biofilms, and other viscous materials. The composition of the present invention can be used to remove any one or more of the contaminants associated with oil recovery, transmission and processing.

In one embodiment, a composition of the subject invention can liquefy solid paraffin at, for example, 25 to 60° C. In some embodiments, the subject invention can also liquefy asphaltenes, asphalts, and resins into more valuable and useful components, such as lighter distillates and/or gas oil fractions, without degrading the crude oil into methane or other undesirable gases. This can be achieved, for example, overnight, i.e., in twelve hours or less. The asphaltenes and resins can, for example, be upgraded into a flammable, soluble form, with advantages over their less flammable solid states.

In certain embodiments, the present invention can be used for the dispersal of precipitated paraffin, asphaltene and/or other contaminating substances, thus allowing for easier and less expensive removal of these contaminants from the crude oil and from equipment.

In one exemplary embodiment, paraffin and/or asphaltene dispersal can be achieved by applying between about 200-600 gallons of treatment into the annulus between the tubing and casing, where it can flow through the pump and into the tubing. The treatment can produce effects in less than 24 hours of shut-in time. Preferably, no shut-in time is required.

In another exemplary embodiment, further well stimulation, i.e., production increases, can be achieved in addition to paraffin and/or asphaltene dispersal. For example, following the application of paraffin and/or asphaltene dispersal treatment, from 15 to 1,000 BBLS volume of the subject treatment can be applied into the annulus between the tubing and casing, where it can then be displaced into the formation. Formation porosity, permeability and thickness can determine the volumes of treatment used. After a shut in time of approximately 3 days, viscosity and interfacial tension are reduced, thus leading to more drastic production increases.

Advantageously, the subject invention can be applied during all stages of the chain of operations, including exploration and production (E&P) operators (e.g., onshore and offshore wellbores, flowlines, and tanks), midstream (e.g., pipelines, tankers, transportation, storage tanks), and in refineries (e.g., heat exchangers, furnaces, distillation towers, cokers, hydro crackers).

In one embodiment, the subject invention can be used for preventing paraffin and asphaltene precipitation and/or deposition from occurring. Dispersal, or dissolution, of precipitates decreases the concentration of contaminants available in the oil to deposit on or in the oil and gas equipment. Thus, the present invention allows for delaying or completely removing the necessity for preventative maintenance related to removing precipitates and deposits, as well as the need for replacing or repairing equipment parts.

In a specific embodiment, the subject invention can be used to disperse asphaltene precipitate in refining operations. High temperatures and vacuum conditions lead to coking, fouling and catalyst deactivation during processing or upgrading of crude oil. To reduce the great expense of, for example, cutting out piping and/or exchanger bundles where precipitation occurs. Other areas of preferential asphaltene precipitation include heat exchangers, furnaces, distillation towers, cokers, hydrocrackers, etc.

In one embodiment, the subject invention can be used for treating heavy oil to improve one or more characteristics of the oil. For example, the composition may be applied to formations containing heavy crude oil, thereby reducing the viscosity of the heavy oil. Advantageously, the subject invention can reduce and/or eliminate the need for, and costs associated with, steam injection and other thermal, chemical and mechanical methods of heavy oil extraction. Further reduced or eliminated are the need for diluents (e.g., light or refined crude oil) and water jackets to help move heavy crude through pipelines. Even further, with the reduction of heavy oil viscosity, transportation of oil is less complicated and/or costly, as the need for tanker trucks and storage tanks is reduced and the use of pipeline transport becomes more feasible.

Moreover, the composition can be applied to an oil formation containing undesirable concentrations of hydrogen sulfide. In one embodiment, the methods can be used for suppressing or eliminating sulfate reducing bacteria, reducing the production of hydrogen sulfide and microbial induced corrosion (MIC), and converting sour oil to sweet oil (or even preserving sweet oil).

The composition can further be applied for the dispersal of paraffinic sludge and scale buildup without need for mechanical cleaning solutions or toxic solvents, for example, in storage and transportation tanks, tankers, ships, trucks, pipelines and flowlines. Methods of cleaning tanks are provided, which can be effective for dispersing sludge and paraffin buildup in a matter of days, for example, less than a week.

In one embodiment, methods of cleaning a storage or transportation tank are provided, wherein air or methane is injected under pressure into a tank, followed by injection of the subject microbe-based composition. Additionally, the method can further comprise pumping any waste water to a treatment plant after treatment with the subject composition. Preferably, the air or methane is injected into the tank to allow for approximately 10 minutes of roiling.

The methods for removing paraffins, asphaltenes, and other contaminants, the dispersal of asphaltene and paraffin precipitates in oil, and the reduction of viscosity and hydrogen sulfide in oil and gas, can be achieved together as one combined process with the application of the subject compositions to surfaces of oil processing equipment and/or the oil passing there through. In other words, the equipment may be cleaned simultaneously with the treatment of crude oil.

The gas and oil processing equipment that can be cleaned and decontaminated according to the subject invention includes all types and varieties of equipment associated with gas and oil recovery, transmission, transportation and processing. This includes, for example, gas and oil well casings, pumps, rods, pipes, lines, tanks, and the like. It is contemplated that the present composition may be used with all such equipment.

In certain embodiments, the compositions used in the methods of the subject invention contain ingredients in amounts effective to clean equipment and/or to provide an effective treatment to inhibit solids buildup. There are multiple ways that the method of removing or preventing contaminant buildup in gas and oil wells and equipment may be implemented using a composition in accordance with the present invention.

In addition to cleaning the wells and associated equipment, it is often desirable to introduce the composition, through perforations in the casing, into the surrounding formation. The composition may be forced into the surrounding formation by applied pressure or, if the composition is allowed to set at the bottom of the casing, the composition may seep into the formation without additional pressure. The composition permeates the formation, dissolving blockages in the formation to provide more efficient oil and gas recovery.

In one embodiment, a method of cleaning and maintaining a working well, including the surrounding formation, includes the steps of pouring or injecting the composition down the casing side (back lines) of a well and allowing it to mix with the fluid that is already in the well. When enough fluid is present, the composition can then optionally be circulated by, for example, a pump for 24-72 hours, preferably 48-72 hours. Prior to circulating, the composition may be allowed to set for 8 to 24 hours, for example. The setting time, circulating time and dosage depend on the amount of paraffin, asphaltene, biofilm, scale, and/or other contaminant anticipated to be present, as well as the depth and size of the well. A basic initial dosage can be, but is not limited to, 20 gallons of composition and for maintaining a clear structure, at least about 5 gallons of composition per well on periodic basis, e.g. biweekly, monthly, bimonthly.

In additional embodiments, the composition of the subject invention may be applied directly to equipment. For example, prior to placing rods and casings into gas and/or oil wells, these parts may be sprayed with, or soaked in, the composition. The parts may be dipped into tanks filled with the composition to prevent corrosion and buildup of contaminants.

The composition may be introduced by means of injection pumps into off-shore gas or oil wells to reduce contaminants, particularly paraffin, in well casings and transmission lines. In addition to the problems associated with land oil wells, off-shore wells have the further problem of the ocean or sea water behaving as a coolant of the lines and contents between the bottom of the ocean and the platform. Thus off-shore wells have a particular problem with paraffin buildup. To treat the lines, from 1-500 gallons up to 1000 barrels, 10,000 barrels, or more, for example, of the composition can be applied to the composition at an injection rate of, for example, 1 to 20 gallons per minute, or 1 to 20 barrels per minute.

The subject treatment can be effective in a range of different geologic formations, as shown in FIG. 21. For example, the subject invention can be useful in formations as deep as about 7,000 feet or deeper, and as shallow as about 1,500 feet or shallower. Additionally, the invention can be useful in formations having a range of porosity and/or permeability, for example from about 0.1% to about 20% or more. The invention can also be useful in formations having a wide range of temperatures, pH, and salinity.

The microbe-based products used in the methods of the claimed invention can contain ingredients in amounts effective to clean the wells, formations, and equipment, to provide an effective coating on their surfaces to prevent future buildup of contaminants, scale and corrosion, and/or to reduce the viscosity of the crude oil to a desired level.

The microbe-based product may be applied with a composition that promotes adherence of the microbe-based product to a surface to be treated. The adherence-promoting substance may be a component of the microbe-based product or it may be applied simultaneously with, or sequentially with, the microbe-based product. Adherence-promoters can include organic or inorganic particles, ions such as calcium, magnesium, phosphate, and sodium, iron, carbon sources that are metabolized to acetyl coenzyme A, acetyl phosphate, and acetate.

Up to, for example, 50 wt. % or more of additives may be added, as needed, for particular applications, such as to vary the VOC levels, increase penetration of the mixture, decrease viscosity of the mixture, as couplers for solvent insolubles in the mixture, and to provide solvents for oleophilic and hydrophilic soils.

Suitable additives include terpenes, terpene alcohols, C8-C14 alcohol ester blends, glycols, glycol ethers, acid esters, diacid esters, petroleum hydrocarbons, amino acids, alkanolamines, and amines, preferably, methyl or isobutyl esters of C4-C6 aliphatic dibasic esters and n-methyl-2 pyrolidone.

Examples of terpenes include d-limonene and .alpha. and .beta. pinene and terpene alcohols, including a terpineol. C8-C14 alcohol ester blends include EXXATE 900, 1000, 1200 from Exxon Chemical; glycols include propylene glycol, dipropylene glycol, and tripropylene glycol; and glycol ethers include dipropylene glycol monomethyl ether, propylene glycol monomethyl ether, propylene glycol-n-butyl ether, ethylene glycol monobutyl ether, and diethylene glycol monobutyl ether. Acid esters include methyl oleate and methyl linoleate, and diacid esters include methyl or butyl diesters of glutaric, adipic, and succinic acids. Petroleum hydrocarbons include AROMATIC 100, AROMATIC 150 ISOPAR M, and ISOPAR K.

Amines such as morpholine; 1,3-dimethyl-2-imidazolidinone; 1,3-propanediamine; 2-amino-1,3-propanediol; and 3-amino propanol; as well as alkanolamines such as triethanolamine, diethanolamine, 2-aminomethyl propanol, and monoethanolamine act as dispersants for contaminants and solubilize fatty acids and oils. Amino acids, provide nontoxic alternatives to monoethanolamine, and act as metal chelators. Methyl or isobutylesters of C4-C6 aliphatic dibasic esters and n-methyl-2 pyrolidone are also useful.

Other additives typically used in cleaning compositions may be used, including water softening agents, sequestrants, corrosion inhibitors, and antioxidants, which are added in amounts effective to perform their intended function. These additives and amounts thereof are well within the skill of the art. Suitable water softening agents include linear phosphates, styrene-maleic acid co-polymers, and polyacrylates. Suitable sequestrants include 1,3-dimethyl-2-imidazolidinone; 1-phenyl-3-isoheptyl-1,3-propanedione; and 2 hydroxy-5-nonylacetophenoneoxime. Examples of corrosion inhibitors include 2-aminomethyl propanol, diethylethanolamine benzotriazole, and methyl benzotriazole. Antioxidants suitable for the present invention include (BHT) 2,6-di-tert-butyl-para-cresol, (BHA) 2,6-di-tert-butyl-para-anisole, Eastman inhibitor O A BM-oxalyl bis (benzylidenehydrazide), and Eastman DTBMA 2,5-di-tert-butylhydroquinone.

All additives should have a flash point greater than 100° F., preferably greater than 150° F. and more preferably 195° F. TCC to achieve a final product flash point greater than 200° F.

Use of Microbe-Based Products in Bioremediation

In one embodiment, the compositions and methods of the subject invention can be used for bioremediation of soils, surfaces, waters, or other sites contaminated with hydrocarbons.

Embodiments of the present invention comprise both in situ and ex situ bioremediation methods of contaminated solids, soils, and waters (ground and surface) wherein in situ techniques are defined as those that are applied to, for example, soil and groundwater at the site with minimal disturbance. Ex situ techniques are those that are applied to, for example, soil and groundwater that have been removed from the site via, for example, excavation (soil) or pumping (water).

In situ techniques are generally the most desirable options due to lower cost and fewer disturbances to the environment. In situ treatment may be limited by, for example, the depth of the soil that can be effectively treated. In many soils, effective oxygen diffusion for desirable rates of bioremediation extend to a range of only a few centimeters to about 30 cm into the soil.

In some embodiments of the present invention, an in situ technique involves mechanically spreading a remediation composition of the present invention onto the contaminated surface. This may be performed using a standard spreader or sprayer device. In some embodiments, a single spreading step may complete the application process, wherein all of the components are included in a single formulation. In other embodiments, which use two- or multiple-part formulations, multiple spreading steps may be used. In one embodiment, the bioremediation composition may be rubbed, brushed, or worked into the surface or ground to be cleaned using a mechanical action to work the bioremediation composition into the pores or grains of the surface and/or to spread the bioremediation composition around the contaminated area. In still further embodiments, when applied to solid surfaces, the application of a remediation composition may be subsequently followed by application of a liquid, such as water. The water may be applied as a spray, using standard methods known to one of ordinary skill in the art. Other liquid wetting agents and wetting formulations may also be used.

Further examples of in situ techniques that may be utilized in some embodiments of the present invention include bioventing, biodegradation, biosparging, and bioaugmentation. Bioventing involves supplying air and nutrients through wells to a site of contamination. In some embodiments of the present invention, pressurized air may be used as a pneumatic carrier gas to transport a microbe-based remediation composition of the present invention to subsurface contamination zones, such as water supplies and aquifers.

In situ biodegradation can further involve supplying oxygen and nutrients by circulating aqueous solutions through contaminated soils to stimulate naturally occurring bacteria to degrade contaminants. Some embodiments of the present invention include the infiltration of water-containing nutrients and oxygen or other electron acceptors for groundwater treatment, after application of the solid or liquid bioremediation composition of the present invention.

In situ biosparging typically involves the injection of air under pressure below the water table to increase groundwater oxygen concentrations and enhance the rate of biological degradation of contaminants by the microbes of the current invention or naturally occurring bacteria. Biosparging increases the mixing in the saturated zone and thereby increases the contact between soil and groundwater. The ease and low cost of installing small-diameter air injection points allows considerable flexibility in the design and construction of the system. In some embodiments of the present invention, the pressurized air of a biosparging process may act as a carrier gas to pneumatically convey a powdered and/or liquid remediation composition of the present invention to a subsurface water source, for example an aquifer.

Ex situ techniques typically involve the excavation or removal of contaminated soil from the ground. Examples of ex situ bioremediation techniques that may be used in some embodiments of the present invention include land-farming, composting, biopiles, and bioreactors.

Ex situ landfarming is a technique in which contaminated soil is excavated and spread over a prepared bed and periodically tilled until pollutants are degraded. In addition to applying a composition of the present invention, this method can be used to stimulate indigenous biodegradative microorganisms and facilitate their aerobic degradation of contaminants. In general, the practice is limited to the treatment of superficial 10-35 cm of soil. In some embodiments of the present invention, the remediation compositions of the present invention may be applied to the prepared beds, in at least one application, followed by periodic tillage. The composition may supplement the indigenous microorganisms, potentially resulting in faster and more complete remediation of the pollutants.

Ex situ composting is a technique that involves combining contaminated soil with nonhazardous organic amendments such as manure or agricultural wastes. The presence of these organic materials supports the development of a rich microbial population and elevated temperature characteristic of composting. Similar to the landfarming example described above, in some embodiments of the present invention, compositions of the present invention may be combined with composting methods to create more effective and faster bioremediation of contaminated sites.

Ex situ biopiles are a hybrid of landfarming and composting. Essentially, engineered cells are constructed as aerated composted piles. Typically used for treatment of petroleum hydrocarbon surface contamination, biopiles are a refined version of landfarming that can control physical loss of contaminants by leaching and volatilization. Biopiles provide a favorable environment for indigenous aerobic and anaerobic microorganisms. The present invention is well-suited to supplement and improve bioremediation of contaminants using biopiles.

Bioreactors, including slurry reactors or aqueous reactors, are used for ex situ treatment of contaminated soil and water pumped up from a contaminated plume. Bioremediation in reactors involves the processing of contaminated solid material (soil, sediment, sludge) or water through an engineered containment system. A slurry bioreactor may be defined as a containment vessel and apparatus used to create a three-phase (solid, liquid, and gas) mixing condition to increase the bioremediation rate of soil-bound and water-soluble pollutants as a water slurry of the contaminated soil and biomass (usually indigenous microorganisms) capable of degrading target contaminants. In general, the rate and extent of biodegradation are greater in a bioreactor system than in situ or in solid-phase systems because the contained environment is more manageable and hence more controllable and predictable. In some embodiments of the present invention, the presently disclosed compositions are used to increase the efficiency and reaction rates of contaminant decomposition reactions in bioreactors.

In one embodiment the microbial composition of the subject invention is dispersed in oil-contaminated soil while being supported on a carrier. The carrier can be made of materials that can retain microorganisms thereon relatively mildly and thus allow easy release of microorganisms thus proliferated. The carrier is preferably inexpensive and can act as a nutrient source for the microorganisms thus applied, particularly a nutrient source that can be gradually released. Preferred biodegradable carrier materials include cornhusk, sugar industry waste, or any agricultural waste. The water content of the carrier typically varies from 1% to 99% by weight, preferably from 5% to 90% by weight, more preferably from 10% to 85% by weight. When the water content of the carrier is too low, microorganism survival is difficult. On the other hand, when the water content of the carrier is too high, the resulting carrier exhibits a deteriorated physical strength that makes itself difficult to handle.

Substances that enhance the growth of microorganisms and the production of biosurfactants may also be added to the microbe-based product and/or the treatment site. These substances include, but not limited to, oil, glycerol, sugar, or other nutrients. For example, a carbon substrate that supports the growth of the biosurfactant-producing microorganisms may be added to the composition or the targeted areas. Biosurfactant producing organisms can grow on the substrate to produce biosurfactant in place and control nematodes.

Carbon substrates can include, but are not limited to, organic carbon sources such as natural or synthetic oil including those used frying oil; fat; lipid; wax (natural or paraffin); fatty acids such as lauric; myristic, etc; fatty acid alcohol such as lauryl alcohol; amphiphilic esters of fatty acids with glycerol such as glyceryl monolaurate; glycol esters of fatty acid such as polyethylene monostearate; fatty acid amines such as lauryl amine; fatty acid amides; hexanes; glycerol; glucose; etc. It is preferable to use a water insoluble carbon substrate to encourage production of the biosurfactants.

Although it is not necessary, it may be preferable to spike or amend the carbon substrate with a sufficient amount of specific biosurfactant to initiate the emulsification process and to inhibit or reduce the growth of other competing organisms for the biosurfactant-producing organism.

In one embodiment, the composition comprises a biosurfactant. The composition preferably contains the active components, such as the biosurfactant, at concentration of 0.01 to 90 by weight % (wt %), preferably 0.1 to 50 wt %, and more preferably 0.1 to 20 wt %.

In another embodiment, the composition comprises a mixture of biosurfactants comprising SLP and MEL. The composition preferably contains the active components, the mixture of SLP and MEL, at concentration of 0.01 to 90 by weight % (wt %), preferably 0.1 to 50 wt %, and more preferably 0.1 to 20 wt %. The mixture of biosurfactants can also comprise other glycolipid biosurfactants, such as RLP, as well as lipopeptides, such as surfactin.

Advantageously, natural biosurfactants are able to inhibit the growth of competing organisms and enhance the growth of the specific biosurfactant-producing organisms.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., oil recovery, drilling, mining, waste treatment, park, remediation, or aquaculture facility). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of live microbes, spores, mycelia, conidia or other microbial propagules can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients, pH control agents, and defoaming agents) that makes the system efficient. Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization, have been sporulated or have sat in the supply chain for some time. The microbe-based products of the subject invention are particularly advantageous compared to traditional products wherein cells, spores, mycelia, conidia and/or other microbial propagules have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the broth in which the microbes are grown. If desired, the compositions can have a high density of vegetative cells or a mixture of vegetative cells, reproductive spores, conidia, mycelia and/or other microbial propagules. Advantageously, the compositions can be tailored for use at a specified location. In one embodiment, the microbe growth facility is located on, or near, a site where the microbe-based products will be used.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell- and/or propagule-count product and the associated broth and metabolites in which the microbes are originally grown.

Advantageously, in preferred embodiments, the systems of the subject invention harness the power of naturally-occurring local microorganisms and their metabolic by-products to improve oil production, transmission and/or refining.

The cultivation time for the individual vessels may be, for example, from 1 to 7 days or longer. The cultivation product can be harvested in any of a number of different ways.

Because the microbe-based product is generated on-site or near the site of application, without the requirement of stabilization, preservation, prolonged storage and extensive transportation processes of conventional production, a much higher density of live microorganisms can be generated, thereby requiring a much smaller volume of the microbe-based product for use in an on-site application. This allows for a scaled-down bioreactor (e.g., smaller fermentation tank; smaller supplies of starter material, nutrients, pH control agents, and de-foaming agent, etc.); no reason to stabilize the cells or separate them from their culture broth; and facilitates the portability of the product.

The microbe growth facilities provide manufacturing versatility by their ability to tailor the microbe-based products to improve synergies with destination geographies.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Local microbes can be identified based on, for example, salt tolerance, ability to grow at high temperatures, and the use of genetic identification of the sequences described herein.

In one embodiment, the composition according to the subject invention is obtained through cultivation processes ranging from small (e.g., lab setting) to large (e.g., industrial setting) scales. These cultivation processes include, but are not limited to, submerged cultivation/fermentation, surface cultivation, solid state fermentation (SSF), and combinations thereof.

Further Definitions

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

EXAMPLES

Example 1—Liquefaction of Precipitated Asphaltene Using Star 3+

Fully precipitated and hardened asphaltene from an oil refinery was liquefied using the Star 3+ treatment of the subject invention. As shown in FIGS. 1-6, solutions of Star 3+ (500 ml), 4 g/L purified SLP and ionic liquid were compared with respect to ability to liquefy 100 g of asphaltene precipitate in shaker flasks. As shown in FIG. 7, effectiveness of Star 3 treatment was also compared to that of Star 3+.

As shown in FIG. 8, the flasks were subjected to 5 hours of shaking, after which amounts of asphaltene precipitate were determined.

Example 2—Example Protocol for Fermentation of Bioemulsifying Yeasts

A nutrient medium comprising two carbon sources was used to cultivate yeasts of, for example, the *Wickerhamomyces*, *Pichia*, and/or *Starmerella* clades. The first carbon source was a sugar, such as dextrose or glucose, at a concentration of 20 to 50 g/L. The second carbon source was a hydrophobic carbon source, such as purified canola or vegetable oil, at a concentration of 50 to 100 g/L.

A nitrogen source such as urea or ammonium salts was also added, as well as magnesium, phosphate and potassium sources.

Fermentation occurred for 1 to 5 days. The final concentration of yeasts that can be achieved is from about 0.5 billion to 2.5 billion CFU/mL.

Example 3—Fermentation of *Starmerella bombicola* for Sophorolipid (SLP) Production in a 110 L Reactor A portable, airlift-type, fully enclosed reactor operated by PLC with water filtration, temperature control unit, and an air blower on board is used. The reactor has a working volume of 90 L when growing *S. bombicola* for SLP production.

In preferred embodiments, the nutrients for SLP production are glucose, urea, yeast extract, canola oil, magnesium sulfate, and potassium phosphate.

The reactor is inoculated with 8 liters of liquid culture grown in flasks. The duration of the cultivation cycle for SLP production is 7-8 days, at 25° C. and pH 3.5, with sampling performed twice a day.

The final concentration of SLP is roughly 10% of working volume, in this case about 9 L of product, containing 300-400 grams of SLP per liter.

Example 4—Fermentation of *Wickerhamomyces anomalus* for SLP Production in a 450 L Reactor A movable airlift reactor operated by PLC with water filtration, temperature control unit, and air blower for sufficient aeration is used. The process can be carried out as batch cultivation process. The reactor has a working volume of 400 L when growing *Wickerhamomyces* or *Pichia* for SLP production.

In preferred embodiments, the nutrients for SLP production are glucose, urea, yeast extract, canola oil, magnesium sulfate, and potassium phosphate.

Inoculation of this reactor requires up to 5% liquid seed culture of working volume. The duration of the cultivation cycle is 7 days, at a temperature 25° C. and pH 3.5, with sampling performed twice a day.

The final concentration of SLP is roughly 20-25% of the working volume, in this case greater than 90 L of product forms.

Example 5—Fermentation of *Wickerhamomyces anomalus* for Cell and Single Cell Protein Production in 900 L Reactor A portable reactor divided into two tanks run by a central airlift to help mix the two tanks simultaneously is used. The reactor has a working volume of 600 L when growing *Wickerhamomyces* and/or *Pichia* for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach 90 kilos per cycle with protein concentration up to 45 kilos.

Example 6—Fermentation of *Wickerhamomyces anomalus* for Cell and Single Cell Protein Production in 2000 L Reactor A portable reactor divided into two square tanks accompanied with 2 loops for mass exchange between them is used. The reactor has a working volume of 750 L when growing *W. anomalus* for cell production.

In a preferred embodiment, the nutrients for cell production are glucose or baking sugar, urea, yeast extract, magnesium sulfate, and potassium phosphate.

The reactor is inoculated with 2% of seed culture. Fermentation continues for 48-72 hours with no pH stabilization, and a temperature of 26 to 32° C.

The final concentration of cells will be 100 g of wet weight per liter. Wet biomass concentration can reach 200 kilos per cycle with protein concentration up to 100 kilos.

Example 7—Fermentation of *Starmerella bombicola* for SLP Production in Portable 14 L Reactor This reactor is an autoclavable jacketed glass vessel with air spurge and impeller. It is equipped with dissolved oxygen, pH, temperature, and foam probe; it has an integrated control station with a color touchscreen interface, built-in pumps, gas flow controllers, and pH/DO foam/level controllers. The working volume of the reactor is 10 liters.

Nutrient medium contains glucose, yeast extract, urea, and vegetable oil. Inoculum can be a 1 to 2-day old culture of *S. bombicola* at about 5-10% of the total culture volume. Cultivation duration and readymade product collection continues for 5-14 days. Final SLP production can reach 1-2 kilogram per cycle.

Example 8—Fermentation of *Pseudozyma aphidis* for Mannosylerythritol Lipid (MEL) Production in Portable 14 L Reactor This reactor is a steam autoclavable jacketed glass vessel with air spurge and Rushton impeller. It is equipped with DO, pH, temperature, and foam probe. It has an integrated control station with a color touchscreen interface, built-in pumps, gas flow controllers, and pH/DO foam/level controllers. The working volume of the reactor is 10 liters.

Nutrient medium composition: Sodium nitrate, Potassium phosphate, Magnesium sulfate, yeast extract, and vegetable oil. Inoculum can be a 1 to 2 day old culture of *Pseudozyma aphidis*, at about 5-10% of the total culture volume. Cultivation duration and sample collection occurs at 9-15 days. Final MEL production can reach 800-1000 grams.

We claim:

1. A method for softening, liquefying and/or removing paraffin and/or asphaltene deposits that have accumulated on a surface within an oilfield pipeline, storage tank, or tubing, wherein said method comprises applying to the pipeline, storage tank, or tubing a composition comprising
   - a biosurfactant blend comprising a sophorolipid and one or both of a rhamnolipid and a mannosylerythritol lipid; and
   - isopropyl alcohol in an amount from 2 ml/L to 100 ml/L, wherein the biosurfactant blend further comprises a fermentation medium in which a biosurfactant-producing microorganism was cultivated as well as residual microbial cell matter, and wherein the composition does not comprise live microbes.

2. The method of claim 1, which comprises applying 0.005-0.1 g/L sophorolipid biosurfactant and 2-50 ml/L isopropyl alcohol.

3. The method of claim 1, wherein the asphaltene is dissolved in 12 hours or less.

* * * * *